(12) United States Patent
D'Ambrosio et al.

(10) Patent No.: US 12,263,330 B2
(45) Date of Patent: *Apr. 1, 2025

(54) INTRAVASCULAR BLOOD PUMP WITH INTAKE FILTER

(71) Applicant: ABIOMED, INC., Danvers, MA (US)

(72) Inventors: Ralph Louis D'Ambrosio, Danvers, MA (US); Maxim Daschewski, Aachen (DE); Valentin Neblik, Aachen (DE); Joerg Schumacher, Aachen (DE); Gerd Spanier, Aachen (DE)

(73) Assignee: ABIOMED, INC., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/211,345

(22) Filed: Jun. 19, 2023

(65) Prior Publication Data

US 2024/0017051 A1 Jan. 18, 2024

Related U.S. Application Data

(63) Continuation of application No. 17/166,397, filed on Feb. 3, 2021, now Pat. No. 11,717,669.
(Continued)

(51) Int. Cl.
*A61M 60/135* (2021.01)
*A61M 60/216* (2021.01)
*A61M 60/888* (2021.01)

(52) U.S. Cl.
CPC ........ *A61M 60/135* (2021.01); *A61M 60/216* (2021.01); *A61M 60/888* (2021.01);
(Continued)

(58) Field of Classification Search
CPC ...... A61M 2205/04; A61M 2205/7563; A61M 2207/00; A61M 60/13; A61M 60/135;
(Continued)

(56) References Cited

U.S. PATENT DOCUMENTS

| | | | |
|---|---|---|---|
| 5,921,913 | A | 7/1999 | Siess |
| 6,248,091 | B1 | 6/2001 | Voelker |

(Continued)

FOREIGN PATENT DOCUMENTS

| | | |
|---|---|---|
| CN | 102380135 A | 3/2012 |
| CN | 109069716 A | 12/2018 |

(Continued)

OTHER PUBLICATIONS

International Search Report and Written Opinion for PCT Application No. PCT/US2021/070123, dated Apr. 20, 2021, 12 pp.
(Continued)

*Primary Examiner* — Jon Eric C Morales
(74) *Attorney, Agent, or Firm* — Botos Churchill IP Law LLP

(57) ABSTRACT

An intravascular blood pump has an intake filter that reduces risk of heart tissue being sucked into an intake port of the pump. The filter defines a plurality of apertures, through which blood flows through the filter. The apertures are sized to prevent ingestion, by the input port, of the heart tissue. The filter includes a plurality of generally helical first struts wound about a longitudinal axis of the filter, and a plurality of second struts. The first and second struts collectively define the plurality of apertures therebetween. The struts may be woven filaments, or the apertures may be defined in a thin film (foil) tube, where remaining material between the apertures form the struts.

20 Claims, 17 Drawing Sheets

Related U.S. Application Data

(60) Provisional application No. 62/970,004, filed on Feb. 4, 2020.

(52) U.S. Cl.
CPC . *A61M 2205/04* (2013.01); *A61M 2205/7563* (2013.01); *A61M 2207/00* (2013.01)

(58) Field of Classification Search
CPC .............. A61M 60/216; A61M 60/237; A61M 60/414; A61M 60/808; A61M 60/81; A61M 60/857; A61M 60/888
See application file for complete search history.

(56) References Cited

U.S. PATENT DOCUMENTS

| | | | |
|---|---|---|---|
| 6,544,216 | B1 | 4/2003 | Sammler et al. |
| 6,808,508 | B1 | 10/2004 | Zafirelis et al. |
| 7,022,100 | B1 | 4/2006 | Aboul-Hosn et al. |
| 8,439,859 | B2 | 5/2013 | Pfeffer et al. |
| 8,888,728 | B2 | 11/2014 | Aboul-Hosn et al. |
| 9,327,068 | B2 | 5/2016 | Aboul-Hosn et al. |
| 9,545,468 | B2 | 1/2017 | Aboul-Hosn et al. |
| 9,561,314 | B2 | 2/2017 | Aboul-Hosn et al. |
| 9,597,437 | B2 | 3/2017 | Aboul-Hosn et al. |
| 9,789,238 | B2 | 10/2017 | Aboul-Hosn et al. |
| 9,833,550 | B2 | 12/2017 | Siess |
| 9,872,948 | B2 | 1/2018 | Siess |
| 10,238,783 | B2 | 3/2019 | Aboul-Hosn et al. |
| 11,123,541 | B2 | 9/2021 | Corbett et al. |
| 11,717,669 | B2 * | 8/2023 | D'Ambrosio ....... A61M 60/857 600/16 |
| 2003/0187322 | A1 | 10/2003 | Siess |
| 2005/0085772 | A1 | 4/2005 | Zafirelis et al. |
| 2010/0022939 | A1 | 1/2010 | Schima et al. |
| 2010/0185043 | A1 | 7/2010 | Woodard et al. |
| 2010/0268017 | A1 | 10/2010 | Siess |
| 2011/0004046 | A1 | 1/2011 | Campbell et al. |
| 2013/0303969 | A1 | 11/2013 | Keenan et al. |
| 2015/0328383 | A1 | 11/2015 | Corbett et al. |
| 2017/0340791 | A1 | 11/2017 | Aboul-Hosn et al. |
| 2019/0209755 | A1 | 7/2019 | Nix et al. |
| 2019/0328948 | A1 | 10/2019 | Salahieh et al. |
| 2022/0072297 | A1 | 3/2022 | Tuval et al. |

FOREIGN PATENT DOCUMENTS

| | | |
|---|---|---|
| GB | 2239675 A | 7/1991 |
| JP | 2017508552 A | 3/2017 |
| WO | 0117581 A2 | 3/2001 |
| WO | 0174255 A1 | 10/2001 |
| WO | 2005016416 A1 | 2/2005 |
| WO | 2009099644 A1 | 8/2009 |
| WO | 2010008560 A1 | 1/2010 |
| WO | 2010042546 A1 | 4/2010 |
| WO | 2015148284 A1 | 10/2015 |
| WO | 2015175711 A1 | 11/2015 |
| WO | 2018226991 A1 | 12/2018 |

OTHER PUBLICATIONS

International Search Report for PCT Application No. PCT/US2017/049879, dated Nov. 29, 2017, 4 pages.
Thorsten Siess, "Systems Analysis and Development of Intravascular Rotation Pumps for Heart Support," Reports from Biomedical Technology, vol. 6, Shaker Verlag (1999), 199 pages.
Willem Flameng, "Temporary Cardiac Assist with an Axial Pump System," Springer-Verlag Berlin Heidelberg, 1991, 79 pages.
Office Action from Japanese Patent Application No. 2022-547198 dated Oct. 17, 2024 (9 pp.).
Office Action and search report for Taiwanese Patent Application No. 110103908 dated Jan. 6, 2025 (8 pp.).

* cited by examiner

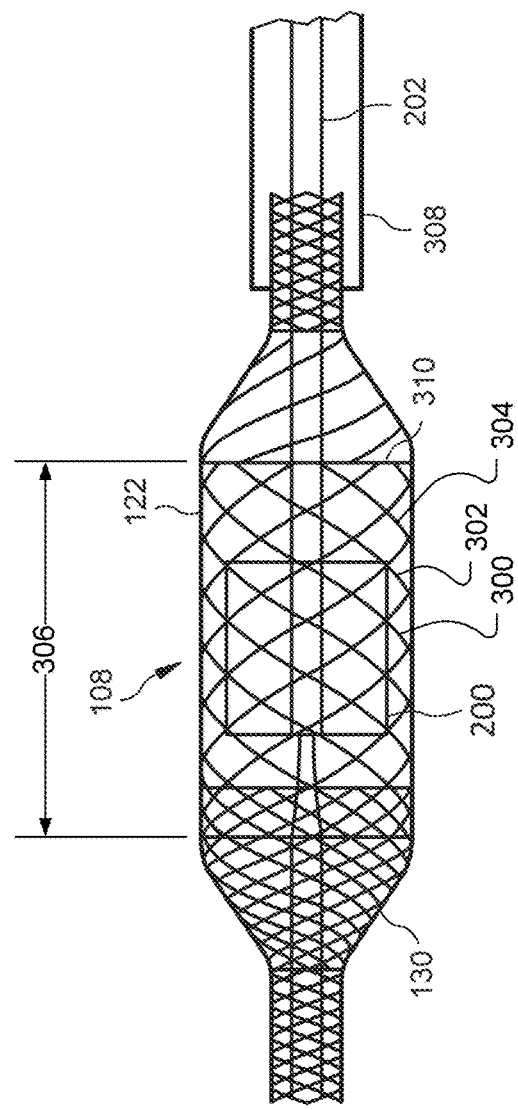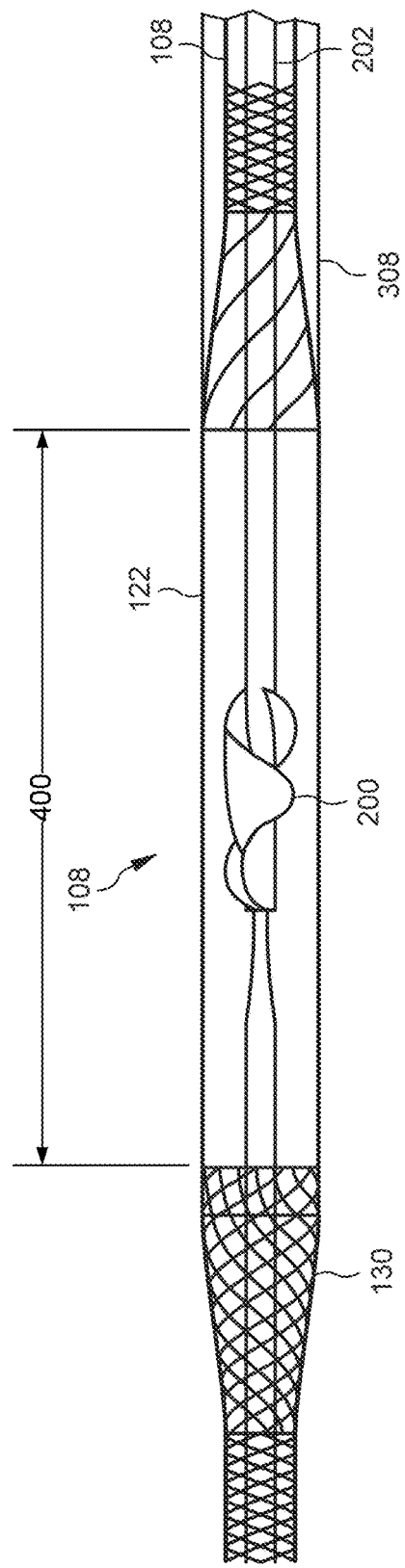
Fig. 3
Fig. 4

INTRAVASCULAR BLOOD PUMP WITH INTAKE FILTER

CROSS-REFERENCE TO RELATED APPLICATION

This application is a continuation of U.S. application Ser. No. 17/166,397, filed on Feb. 3, 2021, now U.S. Pat. No. 11,717,669, which application claims priority to U.S. Provisional Application No. 62/970,004 filed Feb. 4, 2020, the disclosures of all of which are hereby incorporated by reference in their entirety.

TECHNICAL FIELD

The present invention relates to intravascular blood pumps and, more particularly, to intravascular blood pumps that include intake filters.

BACKGROUND

An intravascular blood pump is a pump that can be advanced through a patient's blood circulatory system, i.e., veins and/or arteries, to a position in the patient's heart or elsewhere within the patient's circulatory system. For example, an intravascular blood pump may be inserted via a catheter and positioned to span a heart valve. The intravascular blood pump is typically disposed at the end of the catheter. Once in position, the pump may be used to pump blood through the circulatory system and, therefore, temporarily reduce workload on the patient's heart, such as to enable the heart to recover after a heart attack.

A typical intravascular blood pump includes an impeller disposed within a pump housing. When rotated, the impeller draws blood into an intake port and ejects the blood through an output port. In some cases, the impeller is driven, via a relatively short drive shaft, by an electric motor disposed in the intravascular blood pump. In other cases, the impeller is driven by a relatively long flexible drive shaft that extends through the catheter to a motor external to the patient. In either case, during operation, the impeller and the drive shaft rotate at a relatively high speed.

In use, the intake port may be relatively close to an inside wall of the heart chamber. Consequently, there is a risk that the spinning impeller will draw heart tissue, such as trabeculae carneae or chordae tendineae, into the intake port. Ingesting heart tissue into the intake port may result in damage to the heart tissue, damage to the intravascular blood pump and/or increased risk of blood clots. The heart tissue may become entangled around the drive shaft, which may damage the heart tissue and/or stall the pump. Thus, a technical problem is how to prevent ingesting heart tissue into an intake port of an intravascular blood pump. Accordingly, there is a need for an intravascular blood pump that reduces the risk of heart tissue being sucked into the intake port.

SUMMARY OF EMBODIMENTS

An embodiment of the present invention provides an intravascular blood pump. The intravascular blood pump includes a catheter, a pump housing, an impeller and a filter. The catheter is configured for insertion into a blood vessel. The blood vessel defines an interior volume, through which blood flows. The pump housing is attached to the catheter. The pump housing defines an input port and an output port. The pump housing has a longitudinal axis. The impeller is disposed within the pump housing. The impeller is configured, when rotated, to pump blood from the input port to the output port.

The filter is in fluid communication between: (a) the interior volume of the blood vessel, external to the pump housing, and (b) the input port. The filter includes a plurality of generally helical first struts. The plurality of generally helical first struts is wound about the longitudinal axis. The filter also includes a plurality of second struts. The first and second struts collectively define a plurality of apertures therebetween.

Optionally, in any embodiment, the pump housing, the impeller and the filter may each be alternatingly radially compressible and radially expandable. Optionally, in any embodiment, the pump housing, the impeller and the filter may each be configured to be alternatingly radially compressed and radially expandable.

Optionally, in any embodiment in which the pump housing is compressible, or configured to be compressed, the pump housing is configured, when radially compressed, to longitudinally lengthen an amount that depends on an amount by which the pump housing is radially compressed. In such embodiments, when radially compressed, the pump housing longitudinally lengthens an amount that depends on an amount by which the pump housing is radially compressed. In such embodiments, the filter is configured, when radially compressed, to longitudinally lengthen an amount that depends on an amount by which the filter is radially compressed such that, for a given amount of radial compression, the filter and the pump housing longitudinally lengthen about equal amounts. In such embodiments, when radially compressed, the filter longitudinally lengthens an amount that depends on an amount by which the filter is radially compressed such that, for a given amount of radial compression, the filter and the pump housing longitudinally lengthen about equal amounts Optionally, in any embodiment, the catheter, the pump housing, the impeller and the filter may be configured for use in, or may be used in, a living patient. Each aperture of the plurality of apertures may be sized to prevent ingestion, by the input port, of heart tissue of the living patient.

Optionally, in any embodiment, each aperture of the plurality of apertures may have a largest dimension less than or equal to about 0.5 mm, or less than or equal to about 0.4 mm.

Optionally, in any embodiment, each aperture of the plurality of apertures may have an area less than or equal to about 0.09 $mm^2$, or less than or equal to about 0.16 $mm^2$.

In any embodiment, sizes of the apertures of the plurality of apertures may increase along the longitudinal axis. The increase may, but need not necessarily, be monotonic. The increase may be monotonic.

Optionally, in any embodiment, the first struts may be wound clockwise about the longitudinal axis. The second struts may be generally helically wound counterclockwise about the longitudinal axis.

Optionally, in any embodiment having first generally helically wound first struts, the first struts may be wound in a first direction about the longitudinal axis, and the second struts may be generally helically wound in the first direction about the longitudinal axis. That is, the first and second struts may be wound in the same direction.

Optionally, in any embodiment having first generally helically wound first struts, each strut of at least a subset of the second struts may lie in a respective plane that contains the longitudinal axis.

Optionally, in any embodiment, each aperture of at least a subset of the plurality of apertures may have a general rhombus or rhomboid shape.

Optionally, in any embodiment, the first struts may include a plurality of first filaments. The second struts may include a plurality of second filaments. The first and second filaments may be woven together, such that the plurality of apertures is defined between respective adjacent first and second woven filaments. Although first and second filaments are mentioned, a single continuous filament, such as a single continuous wire, may serve as both the first and second filaments. Different portions of the single filament may serve as the first and second filaments. The different portions need not be contiguous. For example, alternating portions of the single filament may serve as the first filament, and intervening portions of the single filament may serve as the second filament.

Optionally, in some embodiments, the filter includes a tube. The tube has a wall. The plurality of apertures includes a plurality of openings defined through the wall.

Optionally, in any embodiment having a filter that includes a tube, the tube may include a generally funnel-shaped tube.

Optionally, in any embodiment having a filter that includes a tube, the wall may be about 10-100 μm thick.

Optionally, in any embodiment having a filter that includes a tube, the pump housing may include a plurality of third struts. The third struts may collectively define a plurality of third apertures therebetween. At least some of the first and second struts may register radially over respective ones of the third struts.

Optionally, in any embodiment having a filter that includes a tube, each strut of at least a subset of the first struts may include a fork. The fork may include a plurality of tines. A plurality of the first struts and a plurality of the second struts may extend between a pair of the tines and collectively define a plurality of the apertures therebetween.

Optionally, in any embodiment having a forked strut in its filter, each first strut that includes a fork may be wider than each first strut that does not include a fork.

Optionally, in any embodiment having a filter that includes a tube, the apertures may be arranged in a plurality of generally circumferential rows. The rows are circumferential, relative to the longitudinal axis. The rows may be of equal-sized apertures. Ones of the rows may have different numbers of apertures from others of the rows.

Optionally, in any embodiment having generally circumferential rows, a first row of the plurality of generally circumferential rows may include more apertures than a second row of the plurality of generally circumferential rows. Each aperture of the first row may have a smaller area than each aperture of the second row.

Optionally, in any embodiment having generally circumferential rows, the apertures may be arranged in a plurality of generally circumferential bands. The bands may be circumferential, relative to the longitudinal axis. The bands may have about equal-sized apertures. Size of the apertures in each of the plurality of bands may increase along the longitudinal axis. The increase may, but need not necessarily, be monotonic. The filter may include a distal portion and a proximal portion. The distal portion may monotonically increase in diameter in a proximal direction along the longitudinal axis. The proximal portion may monotonically decrease in diameter in the proximal direction along the longitudinal axis. At least a portion of the plurality of apertures may be disposed on the distal portion. In some embodiments, the proximal portion is devoid of apertures.

Optionally, in any embodiment, the first struts and the second struts may be absent any circumferential, relative to the longitudinal axis, struts. Each first strut and each second strut may form a respective non-zero angle with a hypothetical circumferential, relative to the longitudinal axis, ring.

Another embodiment of the present invention provides a method for making a filter for an intravascular blood pump. A catheter is provided. The catheter is configured for insertion into a blood vessel. The blood vessel defines an interior volume through which blood flows. A pump housing is attached to the catheter. The pump housing defines an input port and an output port. The pump housing has a longitudinal axis. An impeller is disposed within the pump housing. The impeller is configured, when rotated, to pump blood from the input port to the output port.

A filter is provided in fluid communication between: (a) the interior volume of the blood vessel, external to the pump housing, and (b) the input port. The filter includes a plurality of generally helical first struts wound about the longitudinal axis. The filter also includes a plurality of second struts. The first and second struts collectively define a plurality of apertures therebetween.

Optionally, in any such method, the filter may include a woven filter.

Optionally, in any such method, the filter may include a shaped tube filter.

BRIEF DESCRIPTION OF THE DRAWINGS

The invention will be more fully understood by referring to the following Detailed Description of Specific Embodiments, in conjunction with the accompanying drawings. The invention will be explained by way of example, with reference to the accompanying drawings. The accompanying drawings are not necessarily drawn to scale. In the drawings, identical or corresponding components illustrated in various figures are represented by the same numeral. For purposes of clarity, not every component may be labeled in every drawing. In the drawings:

FIGS. 3-4 are enlarged side cut-away views of an expandable housing of the intravascular blood pump of FIGS. 1-2, as well as an expandable mesh filter, in an expanded state (FIG. 3) and in a compressed state (FIG. 4), respectively, according to an embodiment of the present invention;

DETAILED DESCRIPTION OF SPECIFIC EMBODIMENTS

Figure 1:
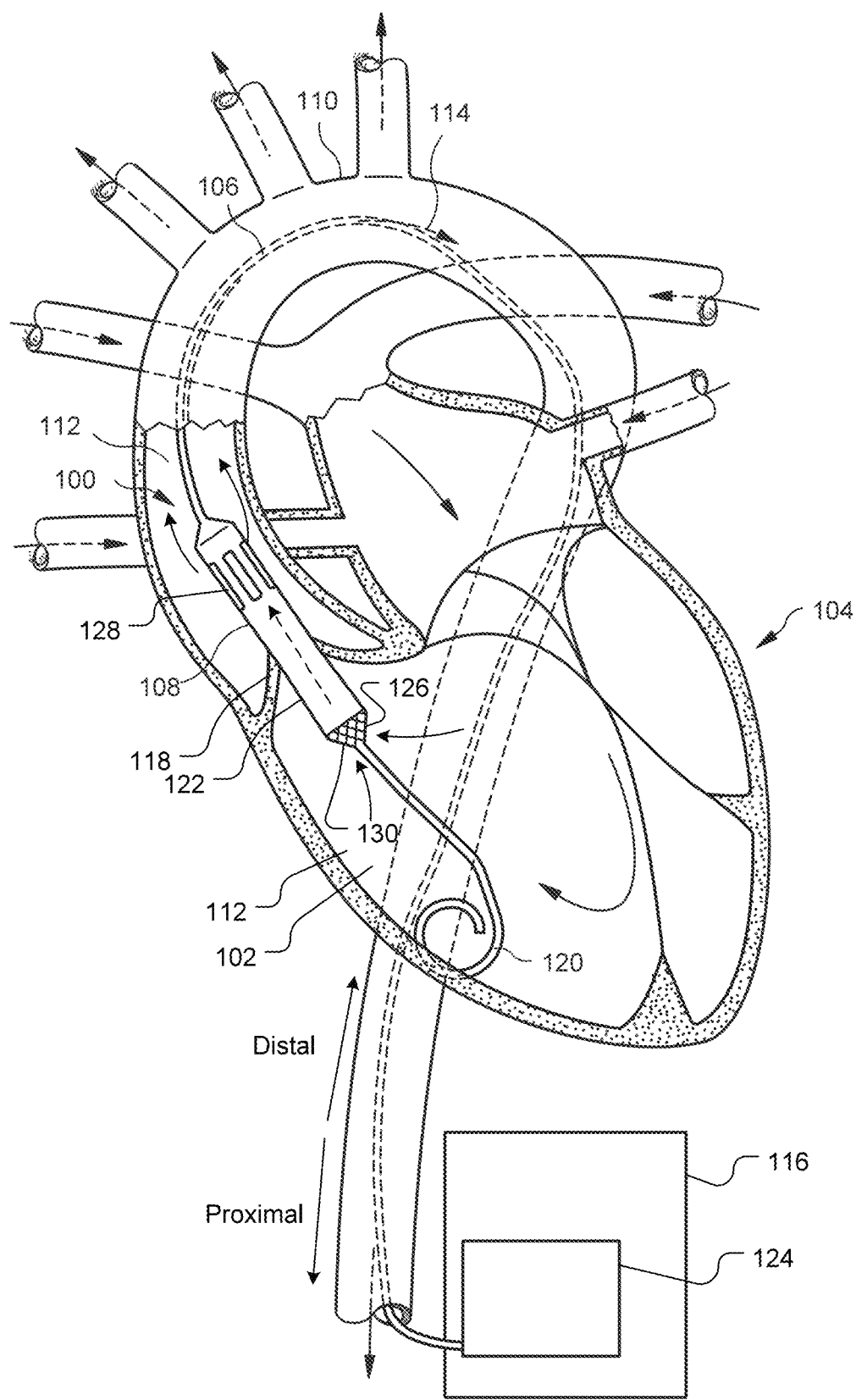
FIG. 1 is a partial cut-away illustration of an intravascular blood pump positioned within a left ventricle of a heart, according to an embodiment of the present invention.

Embodiments of the present invention provide an intravascular blood pump with an intake filter that reduces the risk of heart tissue being sucked into an intake port of the intravascular blood pump. The filter defines a plurality of apertures, through which blood flows through the filter. The apertures are sized to prevent ingestion, by the input port, of heart tissue of a living human or animal patient.

The intravascular blood pump is configured for insertion into a blood vessel of the patient. For example, the intravascular blood pump may be configured for percutaneous insertion into a femoral artery of the patient and to be guided through the patient's vascular system into the heart in order, for example, to support and/or replace pumping action of the heart.

The filter is in fluid communication between: (a) an interior volume of the blood vessel, external to the intravascular blood pump, and (b) the input port. The filter includes a plurality of generally helical first struts wound about a longitudinal axis of the intravascular blood pump. The filter also includes a plurality of second struts. The first and second struts collectively define a plurality of apertures therebetween, and blood is drawn into the input port through the apertures.

In some embodiments, the first and second struts are individual filaments, such as wires, that are woven together in a relatively open weave. In other embodiments, the filter includes a shaped foil tube with the apertures defined therein. The apertures are positioned on the tube, such that material between the apertures forms the first and second struts.

While the present invention is described in the context of an intravascular blood pump having an expandable housing, in which an expandable impeller is housed and driven by an extracorporeal motor via a long and flexible drive shaft, the present invention is also applicable to other types of intravascular blood pumps, such as ones with non-expandable housings and/or ones having motors located inside the patient's body.

Expandable intravascular blood pumps are known, ex., as described in U.S. Pat. Publ. No. 2013/0303969 (the '969 publication) and U.S. Pat. No. 8,439,859 (the '859 patent), the entire contents of each of which are hereby incorporated by reference herein, for all purposes. The '969 publication describes a catheter-pump-assembly. An expandable housing is located at a distal end of the catheter. The expandable housing surrounds an expandable impeller, which is driven by a flexible drive shaft. The drive shaft extends through a first lumen of the catheter. A distal portion of the catheter-pump-assembly may be placed inside the heart via a percutaneous access, for example using the Seldinger technique. The drive shaft contains a central lumen, which may allow a guide wire together with its guide to be passed through the drive shaft to enable an exact positioning of the catheter pump assembly inside the heart. The impeller is rotatably supported in a proximal bearing arranged at the end of the catheter and proximate the impeller.

Expandable Intravascular Blood Pump

FIG. 1 is a partial cut-away illustration of an expandable intravascular blood pump 100 positioned within a left ventricle 102 of a heart 104 of a patient, although in other uses, the expandable intravascular blood pump 100 may be positioned elsewhere in the patient, such as in the left atrium or elsewhere in the patient's vasculature, not necessarily in the heart 104. The intravascular blood pump 100 includes a catheter 106 and a pump section 108 disposed at or near the end of the catheter 106. The catheter 106 is configured for insertion into a blood vessel, such as the aorta 110, that defines an interior volume 112, through which blood flows in a blood flow direction, for example a direction indicated by an arrow 114. As used herein, the term "blood vessel" includes a heart chamber or other lumen. The catheter 106 is connected to a controller 116, such as an Automatic Impella Controller ("AIC") available from Abiomed, Inc., Danvers, MA 01923. The controller 116 provides a user interface for controlling and monitoring the intravascular blood pump 100.

As used herein, the term "distal" refers to a direction or location along the catheter 106 away from the controller 116 or user of the controller 116, and the term "proximal" refers to a direction or location along the catheter 106 toward the controller 116 or user of the controller 116, as indicated by arrows in FIG. 1.

During insertion, the intravascular blood pump 100 may be positioned to extend through the aortic valve 118, as shown in FIG. 1, although in other uses the intravascular blood pump 100 may be positioned elsewhere in a patient's vasculature, not necessarily in the heart 104. Furthermore, although FIG. 1 depicts the intravascular blood pump 100 inserted such that the blood flow direction 114 is away from the distal end of the catheter 106, in other uses the intravascular blood pump 100 may be inserted such that the blood flow direction 114 is toward the distal end of the catheter 106. For example, the intravascular blood pump 100 may be inserted from the left atrium, through the mitral valve, into the left ventricle 102. In the use depicted in FIG. 1, leaves of the aortic valve 118 close around the intravascular blood pump 100.

The intravascular blood pump 100 may be placed inside the heart 104 using a percutaneous, transluminal technique. For example, the intravascular blood pump 100 may be introduced through a femoral artery (not shown). However, alternative vascular access is equally possible, such as access through the subclavian artery. After passing through the femoral artery, the catheter 106 may be pushed into the aorta 110, such that the pump section 108 reaches through the aortic valve 118 into the heart 104. The positioning of the pump section 108 in FIG. 1 serves purely as an example, whereas different placements are possible, such as positioning the pump section 108 inside the right ventricle of the heart 104.

A flexible atraumatic tip 120 having, for example, the form of a pigtail or a J-form extends distally from the pump section 108 distal end. The atraumatic tip 120 should be sufficiently soft to allow the pump section 108 to support itself atraumatically against the inside wall of the left ventricle 102.

The pump section 108 includes an impeller (not visible) disposed inside a housing 122. The housing 122 and the impeller can, but need not necessarily, be expandable. The impeller may be mechanically coupled, via a flexible drive shaft (not shown) that extends through the catheter 106, to an external motor 124. The motor 124 may be in the controller 116 or elsewhere. Alternatively, the impeller may be mechanically coupled via a relatively short drive shaft (not shown) to a motor (not shown) disposed in the pump section 108. In either case, the motor rotates the impeller, via the drive shaft, to cause blood from the interior volume 112 to flow from a blood flow inlet (input port) 126 at a distal end of the pump section 108 to a blood flow outlet (output port) 128 located downstream of the blood flow inlet 126, as indicated by arrows. As noted, the term "interior volume" 112 includes a heart chamber, such as the left ventricle 102.

A filter 130 is disposed in fluid communication between: (a) the interior volume 112 of a blood vessel, in this case the left ventricle 102, external to the pump housing 122, and (b) the input port 126. Although the filter 130 is described in relation to an expandable housing 122 and impeller, the filter 130 may also be used with a non-expandable housing 122 and impeller.

Figure 2:
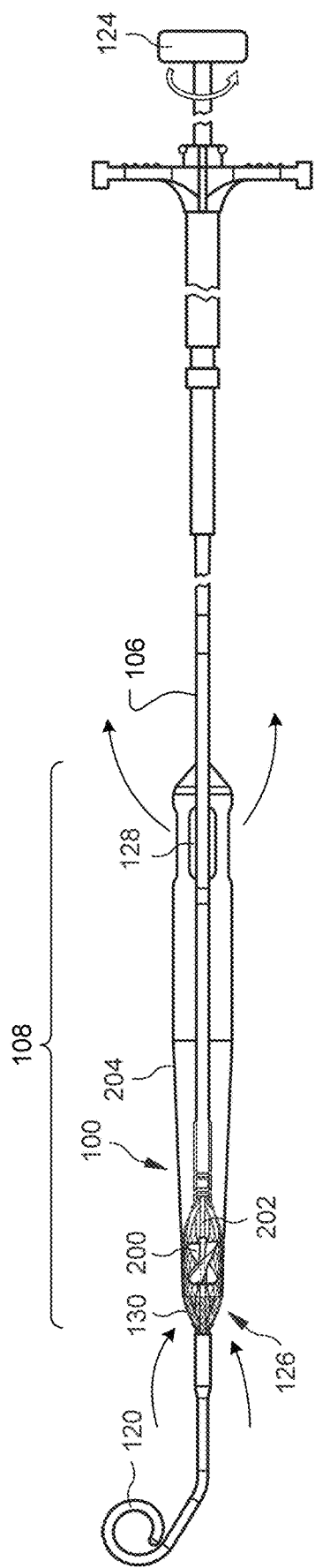
FIG. 2 is a side partial cut-away view of the intravascular blood pump of FIG. 1, including its catheter, according to an embodiment of the present invention.

FIG. 2 is a side, partially cut-away, more detailed view of the intravascular blood pump 100, including the catheter 106. The impeller 200 is shown located inside the housing 122 and mechanically coupled via the flexible drive shaft 202 to the motor 124.

Also shown in FIG. 2 is a limp collapsible outflow hose (downstream tubing) 204 in fluid communication between the output of the impeller 200 and the output port 128. As can be seen in FIG. 1, the pump section 108 is positioned such that the aortic valve 118 closes on the downstream tubing 204. The downstream tubing 204 is sufficiently limp that the aortic valve 118 can collapse the downstream tubing 204 against the catheter 106 when the left ventricle 102 finishes contracting and begins to relax. The closure of the aortic valve 118 prevents blood flowing back into the left ventricle 102.

Conventionally, intravascular blood pumps have not included such downstream tubing. Such a conventional intravascular blood pump therefore has a relatively long intake cannula, upstream of its impeller, to make the intravascular blood pumps sufficiently long to span the heart valve into which it is to be inserted. This length allows for some longitudinal displacement, such as due to heart action and patient movement, without risking displacing the intake and output ports to the same side of the heart valve. Although not consciously designed to do so, such a long intake cannula also makes it almost impossible to damage heart tissue by the impeller. However, such a long intake cannula introduces hydraulic losses, which are particularly problematic in suction lines.

The downstream tubing solves the hydraulic loss problem by enabling the impeller to be positioned much closer to the input port. However, this position of the impeller increases the risk of damage to the heart tissue, and entanglement of the heart tissue around the impeller or drive shaft, which might stall the pump. To avoid this, the filter 130 is disposed on the input port. It has previously been unrecognized that positioning the impeller close to the intake port increases the risk of heart tissue damage or pump stalling.

FIGS. 3 and 4 are enlarged side views of an expandable housing 122 of the intravascular blood pump 100, as well as an expandable filter 130. FIG. 3 shows the expandable housing 122 and the expandable filter 130 in their expanded states, and FIG. 4 shows them in their compressed states. If the housing 122 and the impeller 200 are expandable, the housing 122 may include a plurality of struts, represented by struts 300, 302 and 304, made of a suitable shape memory, hyperelastic or superelastic material, such as Nitinol. Hyperelastic materials are typically elastomers. Many such elastomers can elastically deform up to about 100%. Some superelastic materials can elastically deform up to about 6-8%. Nitinol is a trade name for a nickel-titanium alloy distinguished from other materials by its shape memory and superelastic characteristics.

The struts 300-304 may be made of wire or other filament. As shown in FIGS. 3 and 4, the housing 122 provides a cage around the impeller 200. When radially expanded (FIG. 3), the length 306 of the housing 122 may be less than the length 400 when the housing 122 is radially compressed (FIG. 4). The change in length 400 to 306 may be due to unwinding of the struts 300-304, when the housing 122 expands. In some embodiments, the change in length 400 to 306 may be about 1-2 mm.

The expandable housing 122, expandable impeller 200 and expandable filter 130 may be kept in their compressed states by a suitable compression sleeve 308 slid over the expandable housing 122, expandable impeller 200 and expandable filter 130. The intravascular blood pump 100, with the expandable housing 122, expandable impeller 200 and expandable filter 130, may be transported through the patient's vascular system while the housing 122, impeller 200 and filter 130 are in their compressed states. Once the pump section 108 is at its target location, the housing 122, the impeller 200 and the filter 130 are allowed to expanded, ex., by pushing the pump section 108 out of the compression sleeve 308 in a forward (distal) direction or by pulling back (in a proximal direction) the compression sleeve 308. With the compression sleeve 308 removed, the housing 122 expands, due to its shape-memory, superelastic or hyperelastic properties, as shown in FIG. 3. At the same time, the impeller 200 expands due to its elasticity. As the housing 122 expands radially away from the drive shaft 202, the housing 122 may longitudinally contract to the length 306.

An inside central portion of the housing 122 may have a sleeve or coating 310 (best seen in FIG. 11), which defines a channel, through which the blood is pumped by the impeller 200. Proximally and distally of this channel, the housing 122 allows blood to be sucked into the housing 122 and pushed out of the housing 122 into the downstream tubing 204 (FIG. 2), respectively.

When the intravascular blood pump 100 is in its expanded state and needs to be removed from the patient, the housing 122 is pulled back into the compression cannula 308, which causes the housing 122 to compress radially, and may cause the housing 122 to longitudinally extend to the length 400. The filter 130 and the impeller 200 are also compressed. The smaller diameter of the housing 122 thus achieved facilitates removing the intravascular blood pump 100 from the patient through the vasculature. Thus, the pump housing 122, the impeller 200 and the filter 130 are each configured to be alternatingly radially compressed and radially expanded. Additional details of an expandable intravascular blood pump are provided in the '859 patent.

Figure 5:
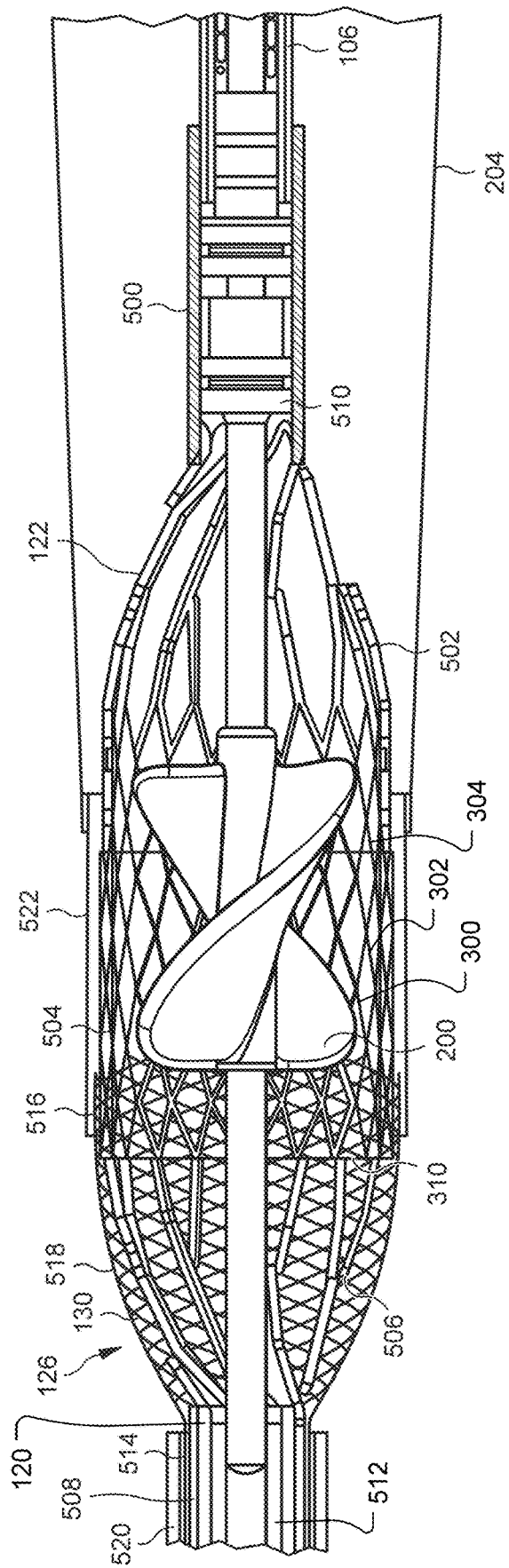
FIG. 5 is a cross-sectional view of the expandable housing and expandable mesh filter of FIG. 3 in the expanded state, according to an embodiment of the present invention.

FIG. 5 is a cross-sectional view of the expandable housing 122 and expandable mesh filter 130 of FIGS. 3 and 4 in their expanded states. The housing 122 includes several parts connected to each other. These parts are, proximally to distally: a proximal tubular housing part 500, a proximal tapered housing part 502, an intermediate tubular housing part 504, a distal tapered housing part 506 and a distal tubular housing part 508. As used herein, "tapered" means having a shape that changes outer diameter smoothly and monotonically, but not necessarily linearly. Thus, in profile, a tapered shape may include convex and/or concave portions. Tapered includes, but is not limited to, conical.

The proximal tubular housing part 500 is attached to the catheter 106 and contains a proximal bearing 510. The proximal tubular housing part 500 has an essentially cylindrical shape. The proximal tapered housing part 502 connects the intermediate tubular housing part 504 to the proximal tubular housing part 500. The intermediate tubular housing part 504 has an approximately cylindrical shape and surrounds the impeller 200. The exact cross-sectional shape of the intermediate tubular housing part 504 may depend on the number of struts 300-304 in the housing 122. In general, the cross-sectional shape may be a polygon, possibly with rounded corners.

The distal tapered housing part 506 connects the intermediate tubular housing part 504 to the distal tubular housing part 508 and defines the blood flow inlet (inlet port) 126 of the housing 122. The proximal tapered housing part 502 has a nearly circular cross-section whose radius increases in the distal direction. As with the intermediate tubular housing part 504, the exact cross-sectional shape of the proximal tapered housing part 502 may depend on a number of struts 300-304 and, in general, the cross-sectional shape may be a polygon, possibly with rounded corners.

Similarly, the distal tapered housing part 506 also has a nearly circular cross-section whose radius, however, decreases in the distal direction. As with the intermediate tubular housing part 504, the exact cross-sectional shape of the distal tapered housing part 506 may depend on a number of struts 300-304 and, in general, the cross-sectional shape may be a polygon, possibly with rounded corners.

The distal tubular housing part 508 contains a distal bearing 512 and is connected to a proximal section of the flexible atraumatic tip 120.

Expandable Filter

Mounted on the outside of the expanded housing 122 and, thus, shown in its expanded state, is the expandable filter 130. The filter 130 includes a distal tubular filter section 514, which has a relatively small diameter, and a proximal tubular filter section 516, which as a larger diameter. As with the intermediate tubular housing part 504, the exact cross-sectional shape of the filter 130, including the exact cross-sectional shape of the distal tubular filter section 514 and the proximal tubular filter section 516, may depend on a number of struts 300-304 and/or a number of struts in the filter 130. In general, the cross-sectional shape may be a polygon, possibly with rounded corners.

A tapered filter section 518 connects the two tubular filter sections 516 and 514. The expandable filter 130 covers: the entire distal tapered housing part 506, i.e. the blood flow inlet (input port) 126, with its tapered filter section 518; some of the intermediate tubular housing part 504 with its proximal tubular filter section 516; and some or all of the distal tubular housing part 508 with its distal tubular filter section 514.

A distal outer foil 520 is arranged on top of the distal tubular filter section 514, which in turn is arranged on top of the distal tubular housing part 508. The distal outer foil 520 may prevent damage to the expandable filter 130, for example, prevent fraying if the expandable filter 130 is made of a mesh of struts. If the distal tubular filter section 514 defines apertures, the distal outer foil 520 may be attached directly to the structure situated underneath the distal tubular filter section 514, such as the flexible atraumatic tip 120, via the apertures. For example, the flexible atraumatic tip 120 and the distal outer foil 520 may be made from the same or similar materials, and the materials may be welded together via the apertures. Since the flexible atraumatic tip 120 is typically made of Polyether block amide (PEBA) or polyurethane, the distal outer film 520 may also be made of PEBA or polyurethane, and the materials may be heat sealed together.

A proximal outer foil 522 is disposed on top of the intermediate tubular housing part 504. The proximal tubular section 516 of the expandable filter 130 is sandwiched between the proximal outer foil 522 and the intermediate tubular housing part 504, albeit only at a distal region of the proximal outer foil 522. The proximal outer foil 522 may prevent damage to the proximal tubular section 516 of the expandable filter 130. In addition, the proximal outer foil 522 is heat sealed to the inside sleeve or coating 310 of the housing 122 through the apertures in the expandable filter 130. The inside sleeve or coating 310 may be made from polyurethane (PU). When the inside sleeve or coating 310 is made of PU, the proximal outer foil 522 is preferably likewise made of PU. When the filter 130 is made with a shaped foil tube that defines apertures, the proximal outer foil 522 may be made integral with the filter 130.

The distal end of the downstream tubing 204 may be attached to a proximal section of the proximal outer foil 522. Alternatively, the downstream tubing 204 may be made integral with the proximal outer foil 522. When the filter 130 is made with a shaped foil tube that defines apertures, the proximal outer foil 522 may be made integral with the filter 130 and the downstream tubing 204.

Helically Woven Filaments Filter

Figure 6:
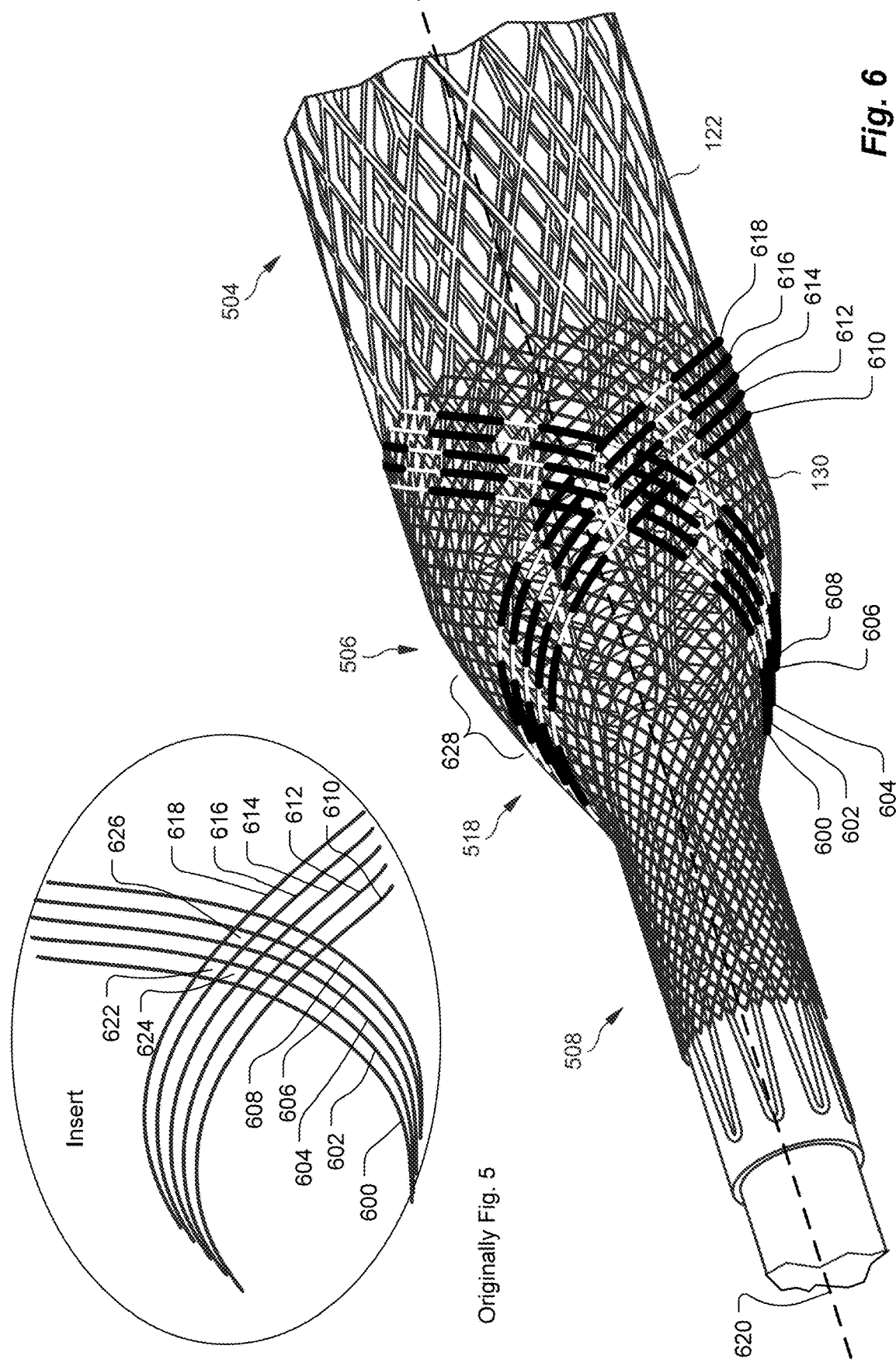
FIG. 6 shows is a perspective view of an expandable filter formed of a mesh of filaments and mounted on a distal end region of the expandable housing (FIGS. 3-5) of the intravascular blood pump of FIGS. 1-2, according to an embodiment of the present invention.

FIG. 6 contains a perspective view of a distal section of the intravascular blood pump 100 with the intermediate tubular housing part 504, the distal tapered housing part 506 and the distal tubular housing part 508. In this embodiment, the expandable filter 130 is a mesh made of filaments that are woven or connected to each other. Weaving is a method of production in which two distinct sets of filaments (warp and weft) are interlaced at angles to form a fabric. The warp is made up of longitudinal filaments, and the weft (or filling) is made up of lateral filaments. The way the warp and weft filaments interlace with each other is called the weave. The majority of woven products are created with one of three basic weaves: plain weave, satin weave or twill.

In plain weave, the warp and weft filaments cross at angles, aligned so they form a simple crisscross pattern. Each weft filament crosses the warp filaments by going over one, then under the next, and so on. The next weft filament goes under the warp threads that its neighbor went over, and vice versa. The filaments of a woven filter 130 are preferably plain woven, although satin, twill or other weaves may be used. Preferably, the mesh is not knitted and contains no loops.

The satin weave is characterized by four or more weft filaments floating over a warp filament, and four or more warp filaments floating over a single weft filament. Floats are missed interfacings, for example where the warp filament lies on top of the weft filaments in a warp-faced satin. The twill weave is characterized by a pattern of diagonal parallel ribs. Twill weave is made by passing the weft filament over one or more warp filaments, then under two or more warp filaments, and so on, with a "step," or offset, between rows to create a characteristic diagonal pattern.

Figure 7:
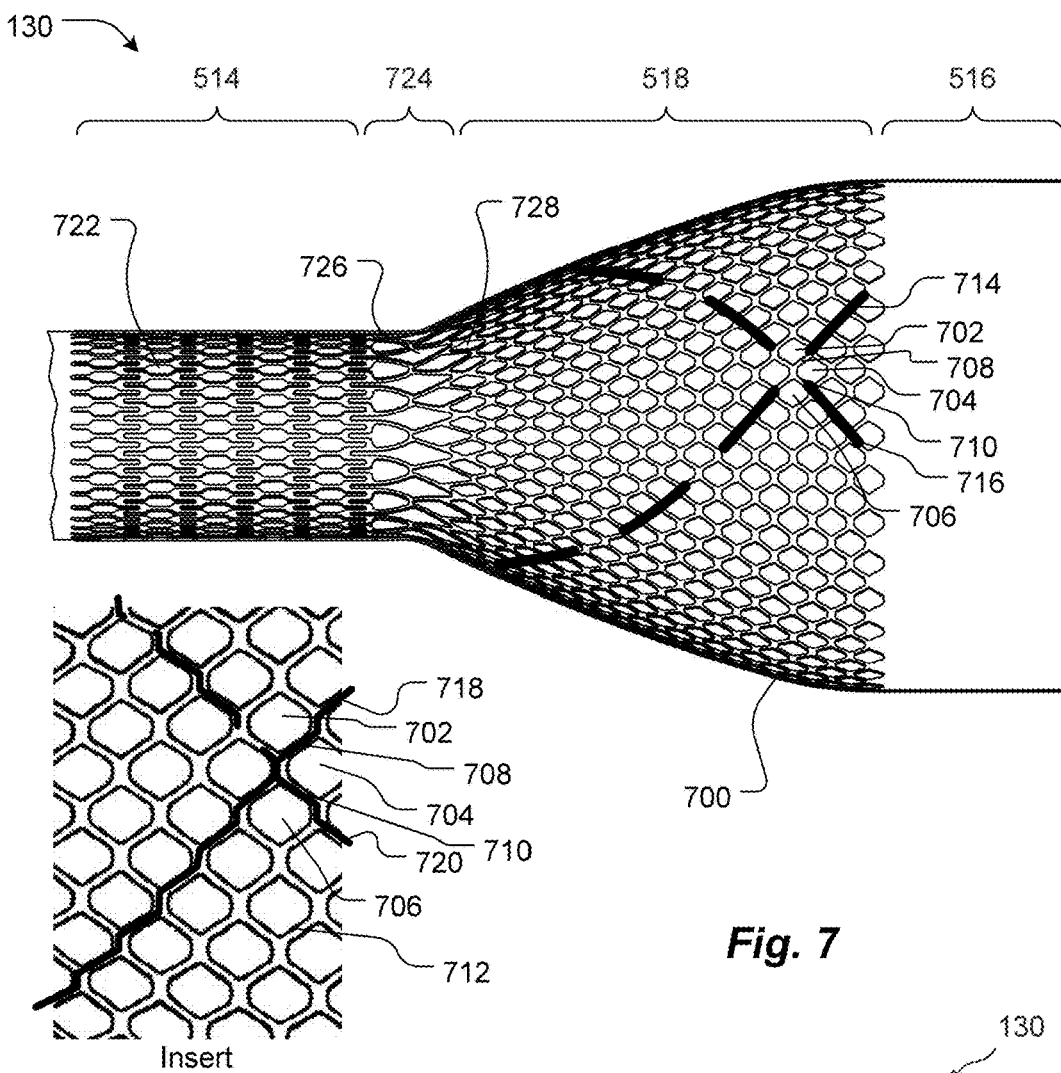
FIG. 7 is a side view, of the expandable filter formed of a filter tube, according to another embodiment of the present invention.

Referring to FIG. 6, the filter 130 may be made of filaments, represented by filaments 600, 602, 604, 608, 610, 612, 614, 616 and 618. The filaments 600-608 are generally helical first struts wound clockwise about a longitudinal axis 620 of the housing 122. As used herein, a "generally helical" curve is a generally smooth space curve. However, as used herein, pitch, radius, curvature and torsion may vary along the length of a helical curve. A helical curve may, but need not, wind more or less than 360° around an axis. Furthermore, a generally helical curve may include minor zigzags, not necessarily all the same, as exemplified by generally helical curves 714 and 716 (FIG. 7).

Returning to FIG. 6, the filaments 610-618 are generally helical second struts wound counterclockwise about the longitudinal axis 620. The filaments 600-618 are indicated by heavy dashed lines, to make them easier to see in the drawing. These filaments 600-618 are also reproduced in an insert in FIG. 6, for clarity. The first struts 600-608 and the second struts 610-618 collectively define a plurality of apertures therebetween, represented by apertures 622, 624 and 626. The first struts 600-608 and the second struts 610-618 are woven together, such that the plurality of apertures 622-626 is defined between respective adjacent first and second woven filaments 600-618.

Each aperture of at least a subset of the plurality of apertures 622-626 may have a general rhombus or rhomboid or rectangular shape. As used herein, a rhomboid is a parallelogram in which adjacent sides are of unequal lengths and angles between adjacent sides are non-right angles. As used herein, a rhombus is a parallelogram in which adjacent sides are equal lengths and angles between adjacent sides are non-right angles. Rhomboids, *rhombi* and rectangles are not necessarily planar. Rhomboids, *rhombi* and rectangles may exist on curved surfaces, as exemplified by apertures 622-626. The sides of a rhomboid, a rhombus or a rectangle need not be perfectly straight, and the sides need not necessarily meet at corners, i.e., there may be a small radius where the two sides meet, for example as discussed in more detail below, with respect to corners in apertures defined by shaped foil tube filters.

In at least a middle portion 628 of the tapered filter section 518, the apertures 622-626 are preferably approximately square shaped. As the diameter of the filter 130 decreases, such as in the distal direction within the tapered filter section 518, the apertures 622-626 may become progressively smaller, and the apertures may become rhomboid shaped, with their long axes extending longitudinally. At the smallest diameter of the tapered filter section 518, the smaller inner angles of rhombus or rhomboid apertures may be less than about 75°.

As the diameter of the filter 130 increases, such as in the proximal direction within the tapered filter section 518, the apertures 622-626 may become progressively larger. At the largest diameter of the tapered filter section 518, the larger inner angles of rhombus or rhomboid apertures may be greater than about 110°. The apertures may become rhomboid shaped, with their long axes extending circumferentially. These numbers correspond to an embodiment in which the larger diameter of the filter 130 is about 2.5 times the smaller diameter of the filter 130. For other ratios of large:small diameters of filter 130, the angles can be adjusted.

The pump housing 122 may be configured, when radially compressed, to longitudinally lengthen an amount that depends on an amount by which the pump housing 122 is radially compressed. The filter 130 may be configured, when radially compressed, to longitudinally lengthen an amount that depends on an amount by which the filter 130 is radially compressed. The filter 130 may be configured such that, for a given amount of radial compression, the filter 130 and the pump housing 122 longitudinally lengthen about equal amounts.

The filaments 600-618 may be a wire, such as Nitinol, suitable polymer, such as polyethylene terephthalate (PET) or PU, fiber or another suitable material. The filament 600-618 material is preferably a shape memory material. Individual filaments 600-618 may have a thickness of between about 10 µm and about 80 µm, or between about 20 µm and about 60 µm, such as about 40 µm. The catheter 106, the pump housing 122, the impeller 200 and the filter 130 are configured for use in a living patient, such that each aperture of the plurality of apertures 622-626 is sized to prevent ingestion, by the input port 126, of heart tissue of the living patient.

In some embodiments where the filter 130 is formed of a mesh, the mesh may be ironed (pressed under heat), prior to attaching the filter 130 to the housing 122. Such ironing may fuse crossing filaments 600-618, particularly if the filaments 600-618 are made of a suitable heat-fusible plastic. Such fused filaments 600-618 form a stronger mesh.

In some embodiments, the woven fabric has a maximum distance between two adjacent filaments 600-618 of between about 0.3 mm (300 µm) and about 0.4 mm (400 µm), when the filter 130 is in the expanded state. In some embodiments, each aperture of the plurality of apertures 622-626 has a largest dimension less than or equal to about 0.5 mm (500 µm), when the filter 130 is in the expanded state. In some embodiments, each aperture of the plurality of apertures 622-626 has a largest dimension less than or equal to about 0.4 mm (400 µm), when the filter 130 is in the expanded state. In some embodiments, each aperture of the plurality of apertures 622-626 has an area less than or equal to about 0.09 mm$^2$, when the filter 130 is in the expanded state. In some embodiments, each aperture of the plurality of apertures 622-626 has an area less than or equal to about 0.16 mm$^2$, when the filter 130 is in the expanded state.

As used herein, "largest dimension" includes a diagonal dimension, such as a dimension between two diagonally opposite corners of a quadrilateral. As used herein, "diameter" of a convex shape means a largest distance that can be formed between two opposite parallel lines tangent to the boundary of the convex shape. As used herein, "width" means the smallest such distance.

Shaped Foil Tube Filter

Figure 8:
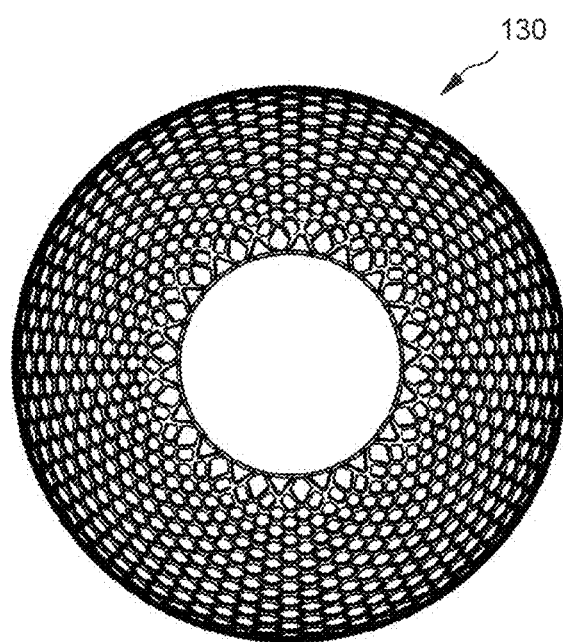
FIG. 8 is an axial (longitudinal) view, of the expandable filter formed of a filter tube, according to another embodiment of the present invention.

FIG. 7 is a side view, and FIG. 8 is an axial (longitudinal) view, of an expandable filter 130 formed of a filter tube. FIG. 7 includes an insert showing an enlarged portion of the expandable filter 130. As noted, in some embodiments, the filter 130 includes a shaped foil tube 700 with the apertures. Examples of the apertures are shown at 702, 704 and 706. An expandable filter 130 that is made from a shaped foil tube 700 is compressed, i.e., radially made smaller, by folding some or all parts of the filter 130. The filter 130 is expanded from its compressed state by unfolding the previously folded parts. Compression and expansion rely primarily on this folding and unfolding, rather than on elastic compression and elongation.

The apertures 702-706 are positioned on the tube, such that material, exemplified by material 708, 710 and 712, between the apertures 702-706 forms first and second struts. Two exemplary struts 714 and 716 are indicated in FIG. 7 by heavy dashed lines. As noted, a generally helical curve may include minor zigzags, not necessarily all the same, as exemplified by generally helical curves 714 and 716. These zigzags are more clearly seen in the insert in FIG. 7, for example in struts 718 and 720, which are indicated by heavy solid and dashed lines.

FIGS. 7 and 8 show the expanded filter 130 as the filter 130 appears when mounted on an expanded housing 122 (ex. FIG. 6), although the housing 122 is not shown in FIGS. 7 and 8. A filter 130 made of a shaped foil tube 700 may be made of a polymer, such as PET or PU. The wall of the foil tube 700 may be about 10 µm to about 100 µm thick, preferably about 15 µm to about 75 µm thick, and more preferably about 20 µm to about 50 µm thick. The thickness of the foil tube 700 wall may decrease continuously in a distal direction in the tapered filter section 518, such as a result of blow mold manufacturing.

Figure 9:
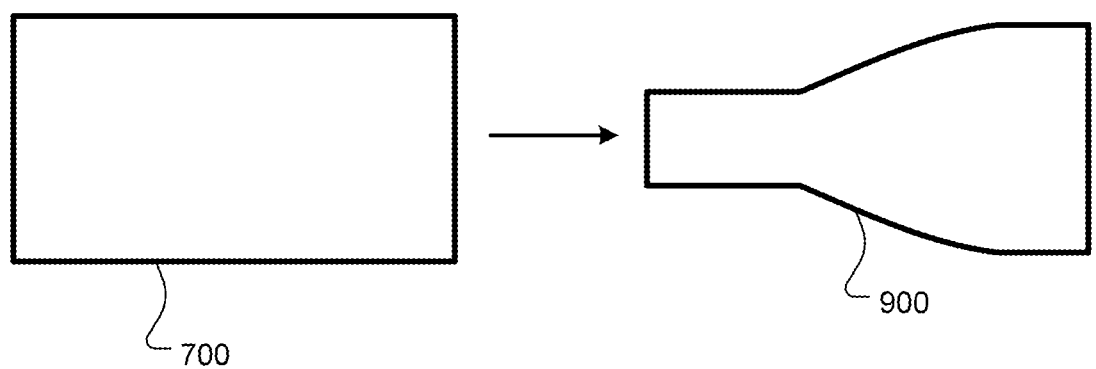
FIG. 9 is a side view illustration of a method for shaping the filter tube of FIGS. 7 and 8, according to an embodiment of the present invention.

As shown in FIG. 9, the foil tube 700 may be shaped on a mandrel 900. The mandrel 900 should have the desired shape of the finished filter 130 in the expanded state. The apertures 702-706 can then be defined in the shaped tube, such as by cutting or punching. The apertures 702-706 may have a general rhombus or rhomboid or rectangular shape. The inside corners of apertures 702-706 in foil tube 700 based filters 130 should have radii of at least about 5 µm, and preferably at least about 20 µm.

Figure 10:
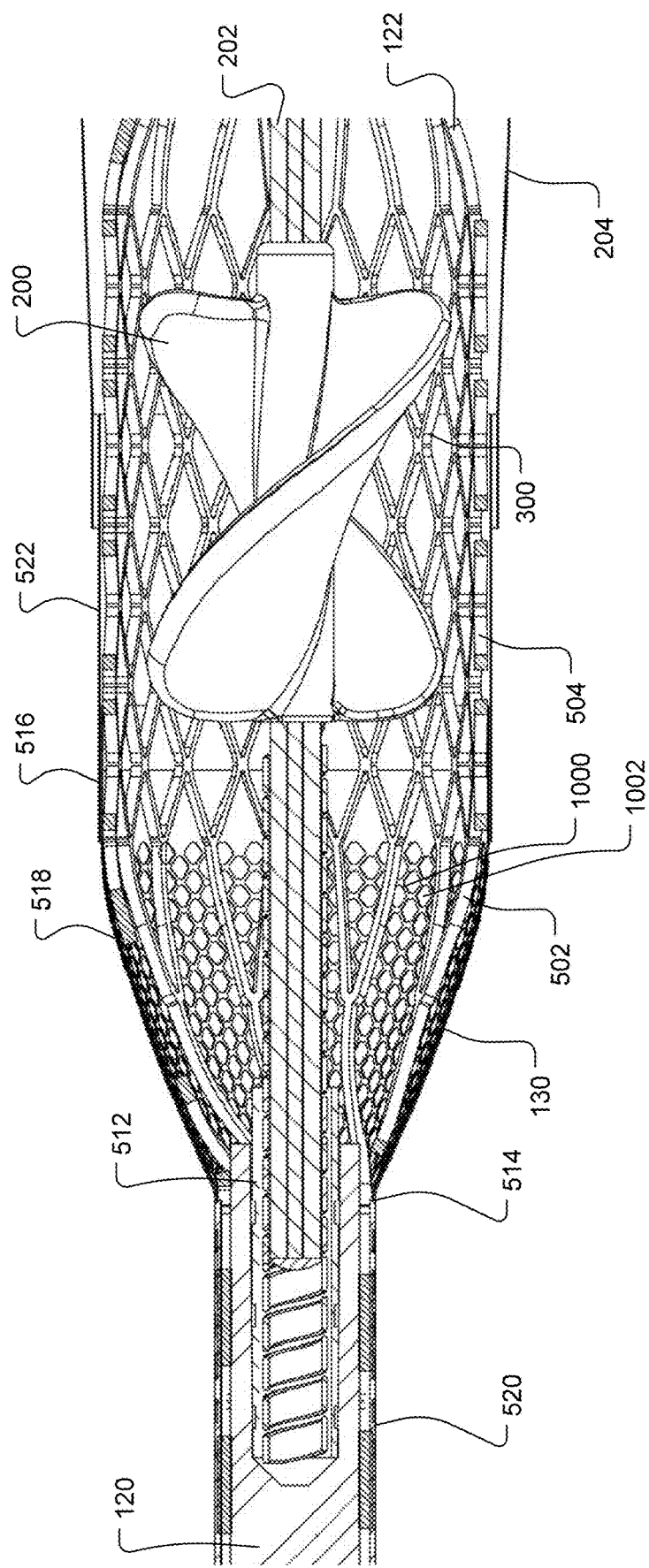
FIG. 10 is a cross-sectional view of the distal end region of the expandable housing of FIGS. 3-5, with the expandable filter of FIGS. 7 and 8 installed thereon, according to an embodiment of the present invention.
Figure 11:
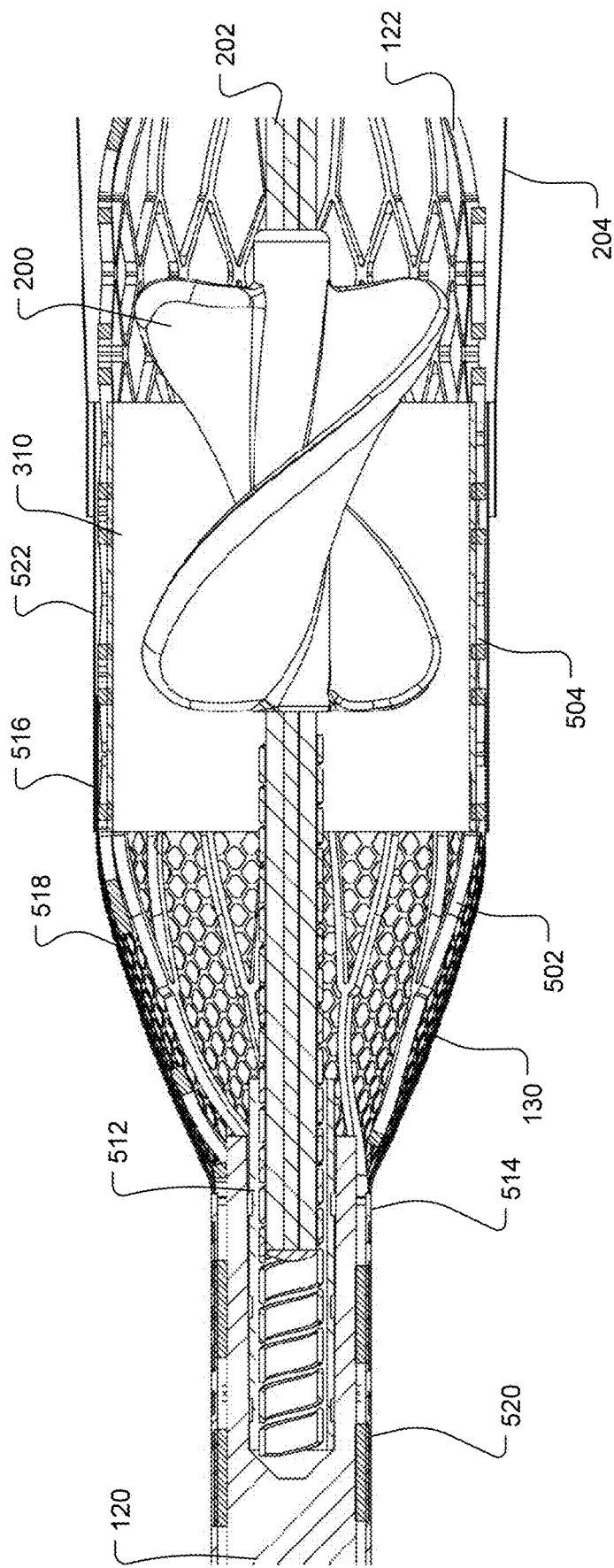
FIG. 11 is a cross-sectional view, as in FIG. 10, however including an expandable housing inner coating, which is not shown in FIG. 10 for clarity, according to an embodiment of the present invention.
Figure 12:
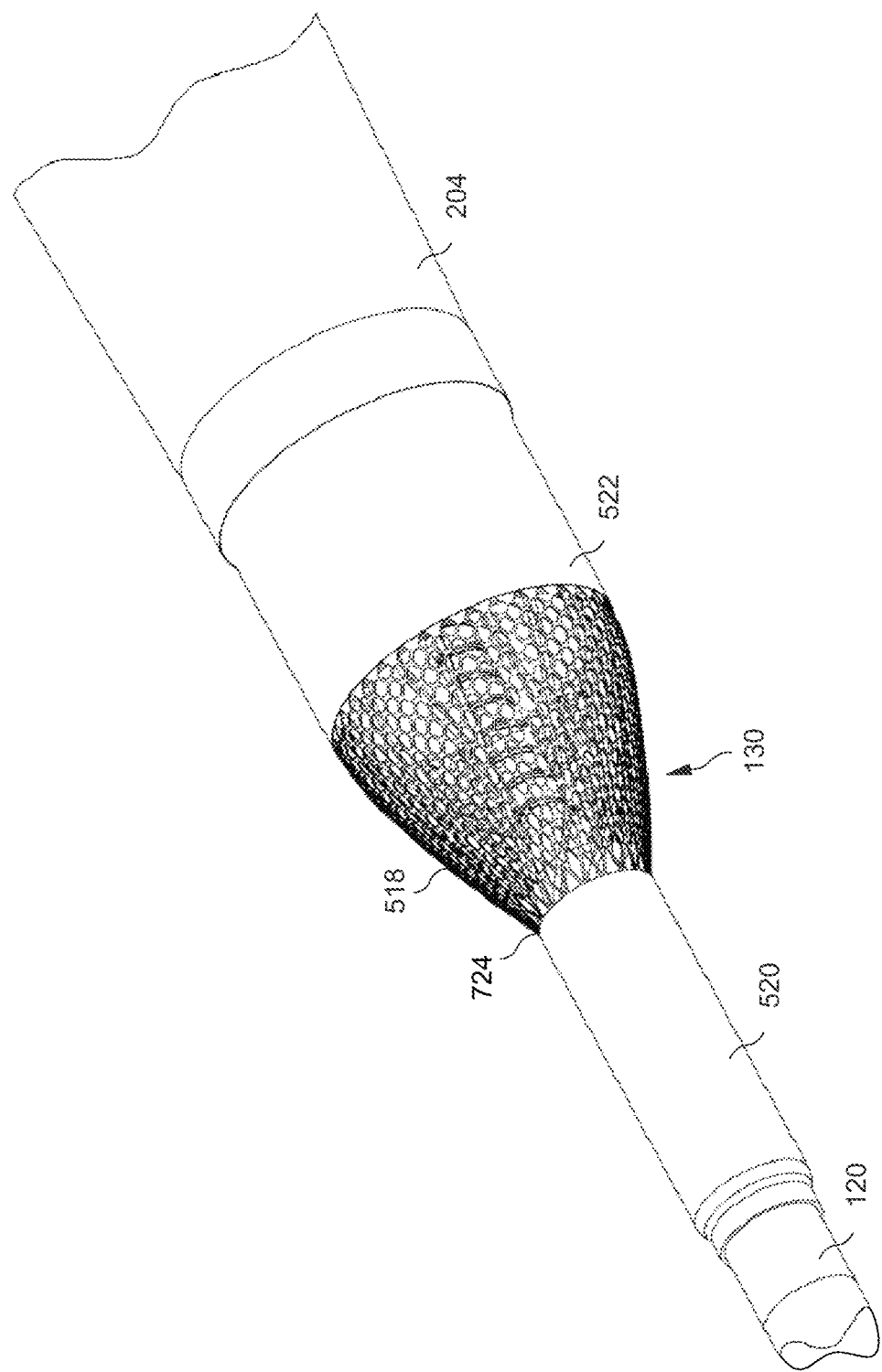
FIG. 12 is a perspective view of the distal end region of the expandable housing of FIGS. 10-11, with the expandable filter of FIGS. 7-9 installed thereon, according to an embodiment of the present invention.

Additional holes may be defined in the shaped tube, such as to facilitate attaching the shaped tube to other components of the intravascular blood pump 100, as discussed herein. The shaped apertured tube can then be installed on the housing 122, as shown in FIGS. 10, 11 and 12. (The housing 122 is not visible in FIG. 12.) FIG. 10 is a cross-sectional view of the distal end region of the expandable housing 122, with the expandable filter 130 installed thereon. FIG. 11 is a cross-sectional view, as in FIG. 10, however including an expandable housing inner coating 310, which is not shown in FIG. 10 for clarity. FIG. 12 is a perspective view of the distal end region of the expandable housing 122, with the expandable filter of FIGS. 7-8 installed thereon.

Returning to FIGS. 7 and 8, the shape and size of the holes may differ in different parts of the expandable filter 130. In the distal tubular filter section 514, the holes, exemplified by hole 722, may be longer (in a longitudinal direction) than wide (in a circumferential direction). The holes 722 may be defined in circumferential rows. Holes 722 in adjacent rows may be staggered in the circumferential direction, and partially overlap in the longitudinal and circumferential directions, as shown in FIG. 7. Such staggering and overlapping enables the distal tubular section 514 to easily dilate during assembly, without requiring resilient stretching of the material. This dilation may facilitate inserting the impeller 200 into the housing 122 through the distal end of the housing 122. Furthermore, such staggering generally enables disposing the holes 722 closer together and, therefore making the filter 130 more transparent to blood flow.

The distal outer foil 520 (FIG. 10) may be heat sealed, such as by welding, through the holes 722 of the distal tubular filter section 514 extend to a proximal section of the flexible atraumatic tip 120. Each hole 722 in the distal tubular filter section 514 has an enlarged portion located centrally in a longitudinal slot. After the insertion of the impeller 200 and the return of the distal tubular section 514 to its normal diameter, the enlarged portion advantageously has a relatively large open contact area for attachment of the distal outer foil 520 to the flexible atraumatic tip 120.

The expandable filter 130 further includes a transitional zone 724 (FIG. 7) where the distal tubular filter section 514 and the tapered filter section 518 meet. Holes, exemplified by hole 726, in the transitional zone 724 are longer and wider than adjacent holes of the tapered filter section 518. Preferably, the holes 726 in the transitional zone 724 are at least twice as large as the adjacent holes, exemplified by hole 728, in the tapered filter section 518. In one embodiment, for each pair of circumferentially adjacent holes 728 in a row of the tapered filter section 518, the transitional zone 724 has one hole 726 that circumferentially straddles the two holes 728. Thus, the number of holes in a circumferential row in the transitional zone 724 is half the number of holes in a circumferential row in the tapered filter section 518. In some other embodiments, other ratios may be used, such as 3:1, 4:1 or 3:2. Each hole 726 in the transitional zone 724 may be about twice, thrice or another multiple as long (in the longitudinal direction) and about twice, thrice or another multiple as wide (in the circumferential direction) as the hole 728 in the tapered filter section 518, depending on the ratio of the number of holes 728 in one row of the tapered filter section 518 to the number of holes 726 in one row of the transitional zone 724.

The dimensions and shapes of the holes 702-706 and 728 and dimensions of the struts 714-716 should be chosen such that, when the tapered filter section 518 is fully open, the housing 122 can be inserted into the tapered filter section 518, without exceeding limits of elastic deformation of the material. For example, the length of two circumferentially adjacent struts 714-716 (on zigzag of a zigzag circumferential ring), multiplied by the number of apertures 702-706 in a circumferential row, should about equal the circumference of a fully-expanded housing 122, taking into account any local elastic deformation of the filter material.

Adjacent holes 726 in the transitional zone 724 are separated from each other by struts that are wider than an adjacent strut 714-716 of the tapered filter section 518. These wider struts stabilize the larger holes 726. When the distal outer foil 520 is placed over of the distal tubular filter section 514, longitudinally proximally up to the transitional zone 724, the distal outer foil 520 at least partially covers, and therefore reduces the effective size of, the first one or more rows of the holes 726 in the transitional zone 724. In some cases, these reduced hole sizes may lead to blood damage or increased risk of clotting. Therefore, the holes 726 in the transitional zone 724 should be chosen to be larger than holes in the tapered filter section 518.

As can be seen in FIG. 7, the holes 728 in a distal region of the tapered filter section 518 are narrower, in a circumferential direction, than the holes 702-706 in a proximal region of the tapered filter section 518. In other words, sizes of the apertures 702-706 increase monotonically in the proximal direction, along the longitudinal axis. In addition, in the distal tubular filter section 514, the holes 722 take the form of narrow axial slits, which are offset from each other in a circumferential direction. This is advantageous, as narrow holes can widen when the expandable filter 130 is expanded at the distal tubular filter section 514 and the distal region of the tapered filter section 518, such as when the impeller 200 is inserted into the housing 122. Wider holes are bounded by thicker struts, particularly in the tapered filter section 518. The struts have a width of between about 30 µm in the distal region, and about 60 µm in the proximal region, of the tapered filter section 518. Preferably, the largest diameter of the holes in the tapered filter section 518 is between about 300 µm and about 500 µm.

In the embodiment shown in FIG. 7, the proximal tubular filter section 516 has no holes. However, holes in the proximal tubular filter section 516 may be desirable, such as when the proximal outer foil 522 is placed over the proximal tubular filter section 516 (FIG. 5), which in turn is situated over the intermediate tubular housing part 504. The proximal outer foil 522 fixes the expandable filter 130 to the housing 122, and since the tubular housing part 504 is coated with PU and the proximal outer foil 522 is also made of PU, they can easily be heat sealed or welded together through such holes. However, if both the filter 130 and the proximal outer foil 522 are made of compatible materials, such as PU, the filter 130 and the proximal outer foil 522 can be directly joined together, such as by applying heat.

When the expandable filter 122 in FIGS. 7 and 8 is disposed on the expanded housing 122, as shown e.g. in FIG. 10, the distal tubular filter section 514 is preferably disposed on top of the distal bearing 512 and the flexible atraumatic tip 120. The distal tubular filter section 514 is covered with the distal outer foil 520 to fasten the expandable filter 130 to the intravascular blood pump 100.

Figure 13:
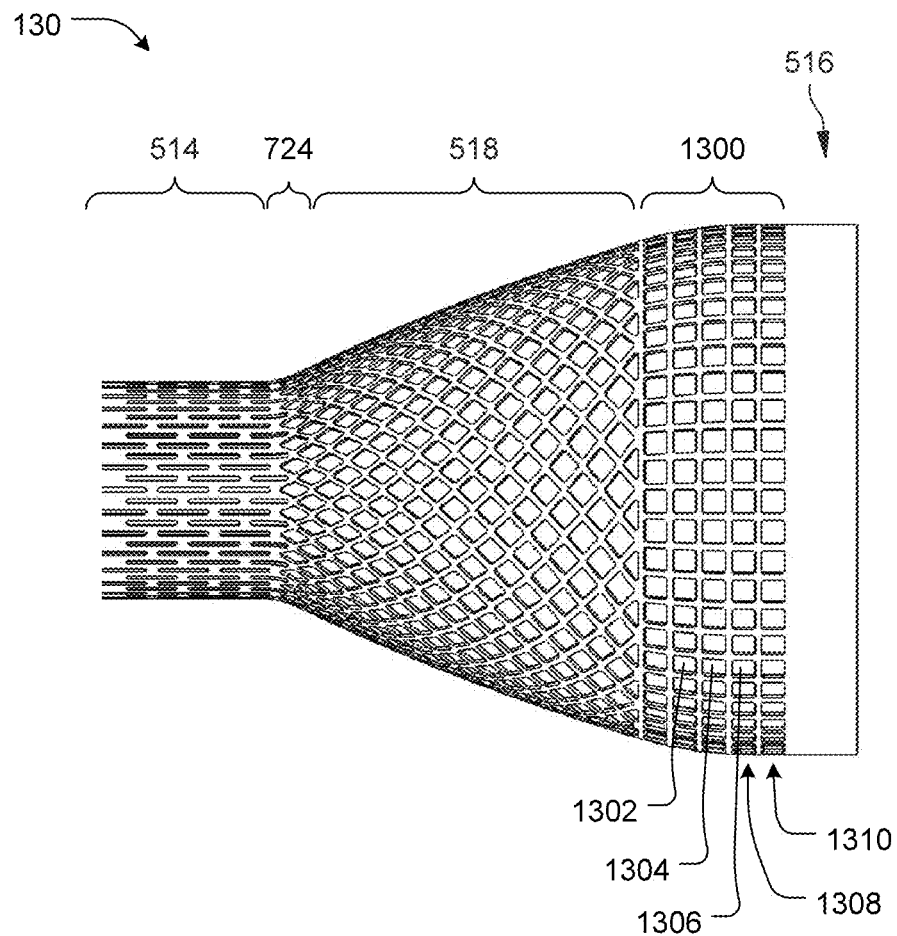
FIG. 13 is a side view of the expandable filter of FIGS. 7-8, according to an alternative embodiment of the present invention.

The proximal tubular filter section 516 has a relatively large diameter. If this diameter is not likely to change significantly during assembly of the intravascular blood pump 100, i.e., the proximal opening of the filter 130 is not likely to be significantly stretched, any holes defined in this section will not be significantly deformed during assembly. Thus, these holes can be square or another shape, and the holes can be at least partially defined by circumferential rings of struts. FIG. 13 shows such an embodiment. FIG. 13 is a side view of the expandable filter 130 of FIGS. 7 and 8, according to an alternative embodiment of the present invention.

The expandable filter 130 of FIG. 13 includes a band 1300 of several parallel rings of holes, exemplified by holes 1302, 1304 and 1306 and rings 1308 and 1310. All the rings 1308-1310 have the same number of holes 1302-1306, and the holes 1302-1306 are largely equal sized. Consequently, the ratio of total hole area to total strut area within the band 1300 is relatively high, compared to other portions of the filter 130. A high hole-to-strut ratio is advantageous, because it makes the filter 130 more transparent to blood flow, which reduces risk of hemolysis and clotting. The ratio of total hole area to total filter 130 area exposed to blood should be at least about 60%, preferably at least about 70% and more preferably at least about 80%. This band 1300 can be combined with the large holes 726 in the transitional zone 724 discussed herein, with respect to FIG. 7.

Descriptions of hole and aperture shape are given for expanded filters 130. When a filter 130 is compressed, such as by folding, the hole shapes may change drastically. Indeed, it is the ability of the struts to bend that makes the filters 130 easy to compress.

Figure 14:
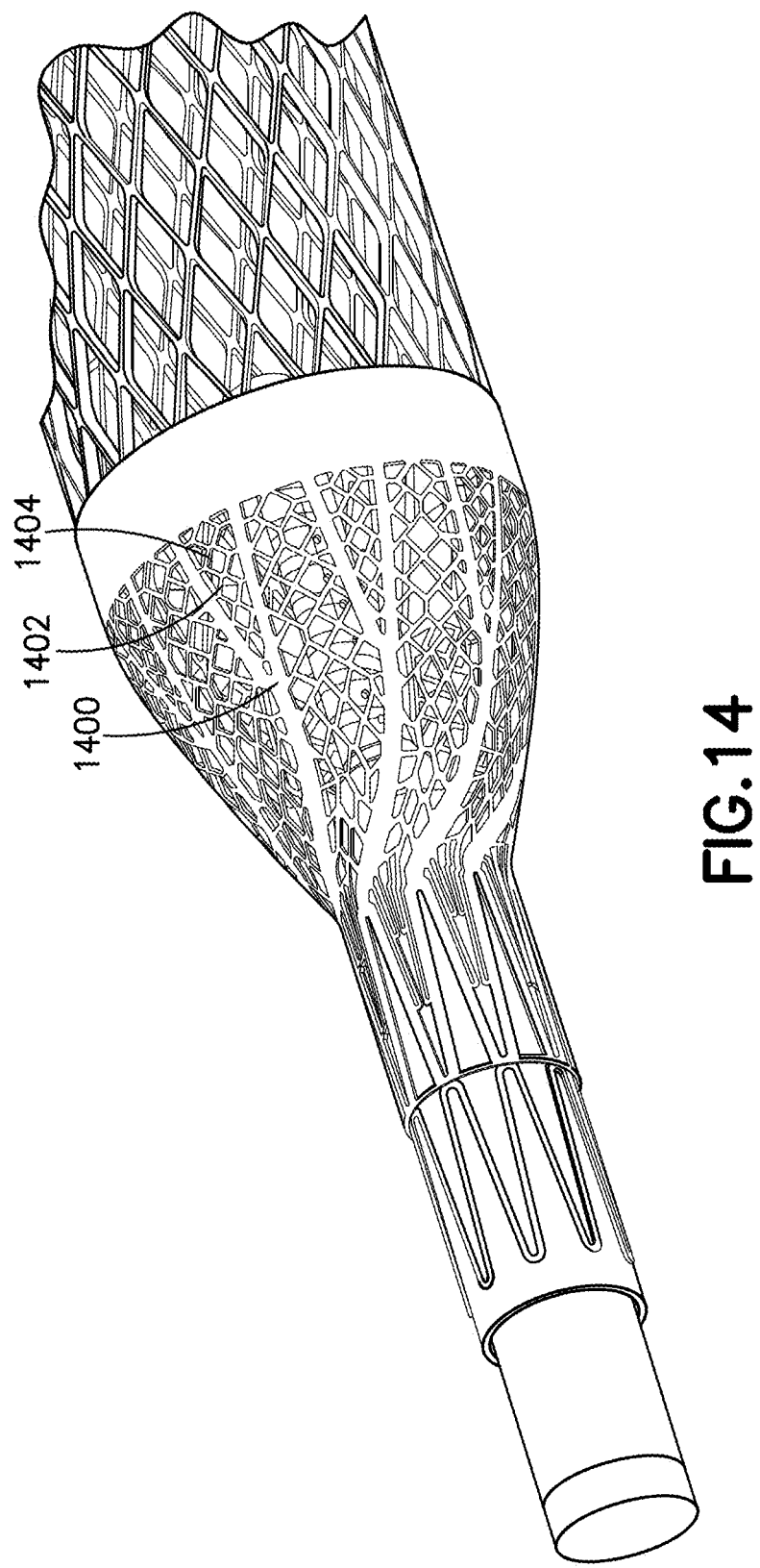
FIG. 14 is a perspective view of the distal end region of the expandable housing of FIGS. 10-11, with an expandable filter similar to that of FIGS. 7-8 and/or 13, but with a different pattern of apertures, installed thereon, according to an alternative embodiment of the present invention.

FIG. 14 is a perspective view of the distal end region of the expandable housing of FIGS. 10-11, with an expandable filter similar to that of FIGS. 7-8 and/or 13, but with a different pattern of apertures, installed thereon. For example, some of the struts are forked, as exemplified by strut 1400. Some of the struts, such as forked strut 1400, may be wider than other struts. Some of the struts, exemplified by struts 1402 and 1404, extend between respective pairs of tines of the forks. Thus, a plurality of the first struts and a plurality of the second struts extend between a pair of the tines and collectively define a plurality of the apertures therebetween. Each first strut that comprises a fork may be wider than each first strut that does not comprise a fork.

Optionally, one or more of the struts may register over respective struts of the housing 122. As shown in FIG. 10, the housing 122 includes struts, represented by strut 300, as discussed with respect to FIGS. 3 and 4. Housing struts 300 are referred to herein as third struts. Groups of these third struts, represented by strut 1000 (FIG. 10), collectively define apertures therethrough, represented by aperture 1002 (FIG. 10). At least some of the first and second struts, i.e., struts in the filter (see FIG. 7), such as the forked struts 1400 (FIG. 14), register radially over respective ones of the third struts for support.

Figure 15:
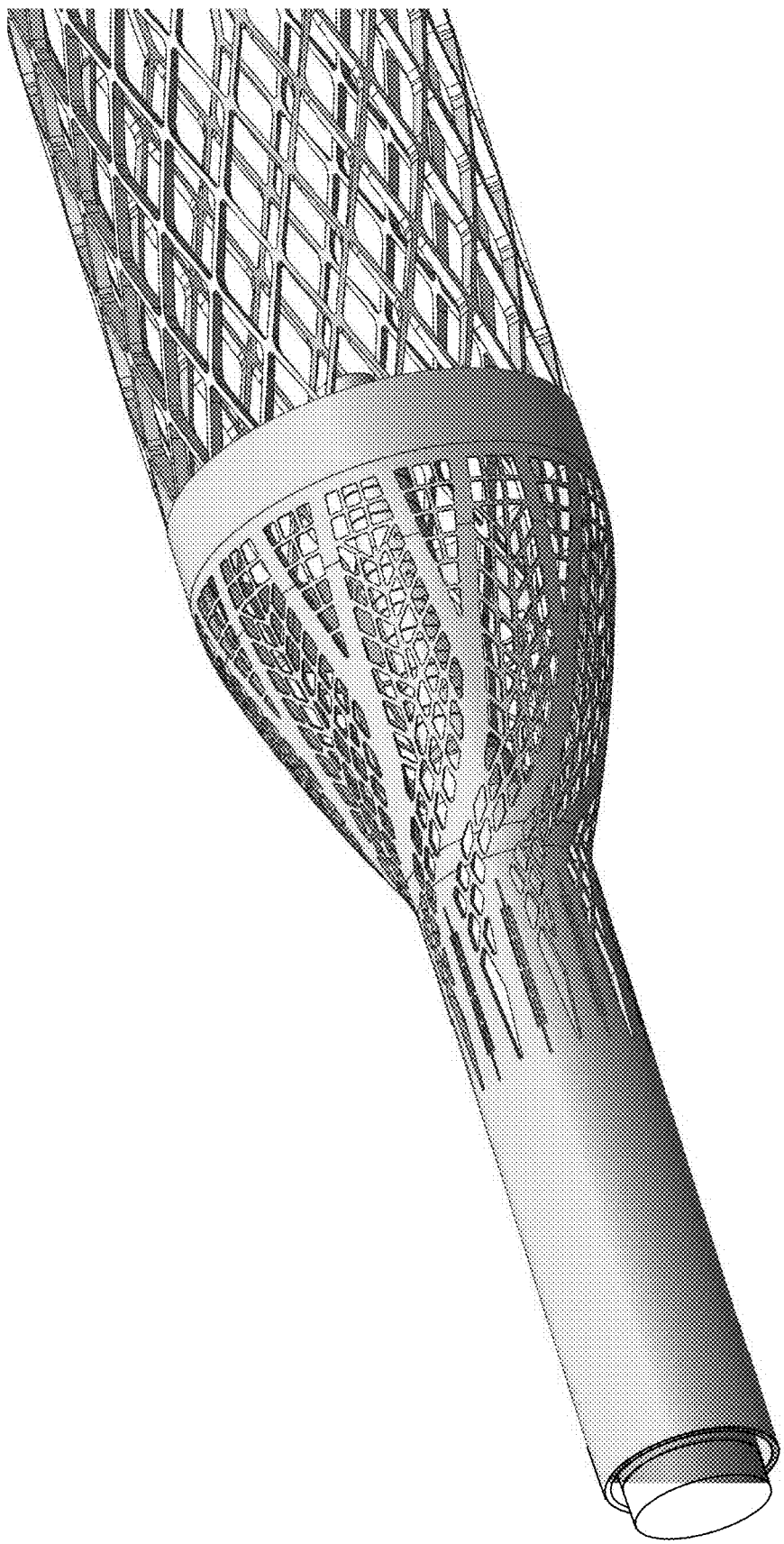
FIG. 15 is a perspective view of the distal end region of the expandable housing of FIGS. 10-11, with an expandable filter similar to that of FIG. 14 installed thereon, but with a further different aperture pattern that is different from the aperture pattern of FIG. 14, according to another alternative embodiment of the present invention.

FIG. 15 is a perspective view of the distal end region of the expandable housing of FIGS. 10-11, with an expandable filter similar to that of FIG. 14 installed thereon, but with a different aperture pattern, according to another alternative embodiment of the present invention.

Figure 16:
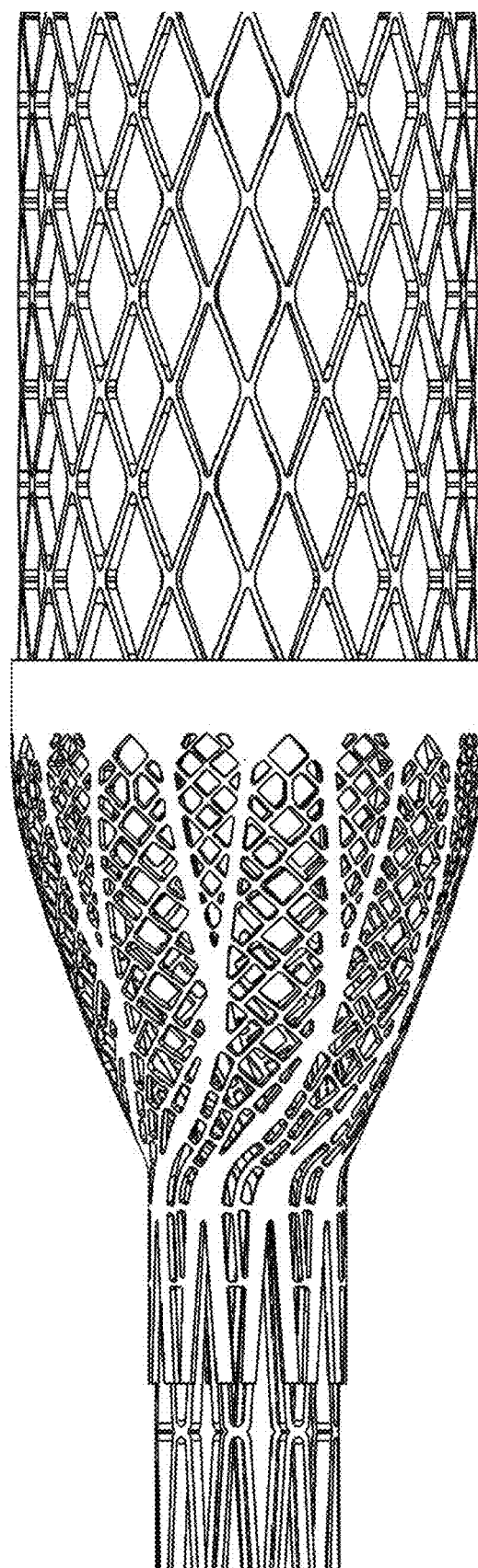
FIG. 16 is a side view of the distal end region of an expandable housing of FIGS. 10-11, with an expandable filter similar to that of FIG. 14 installed thereon, according to yet another alternative embodiment of the present invention.

FIG. 16 is a side view of the distal end region of the expandable housing of FIGS. 10-11, with an expandable filter similar to that of FIG. 14 installed thereon, according to yet another alternative embodiment of the present invention.

Figure 17:
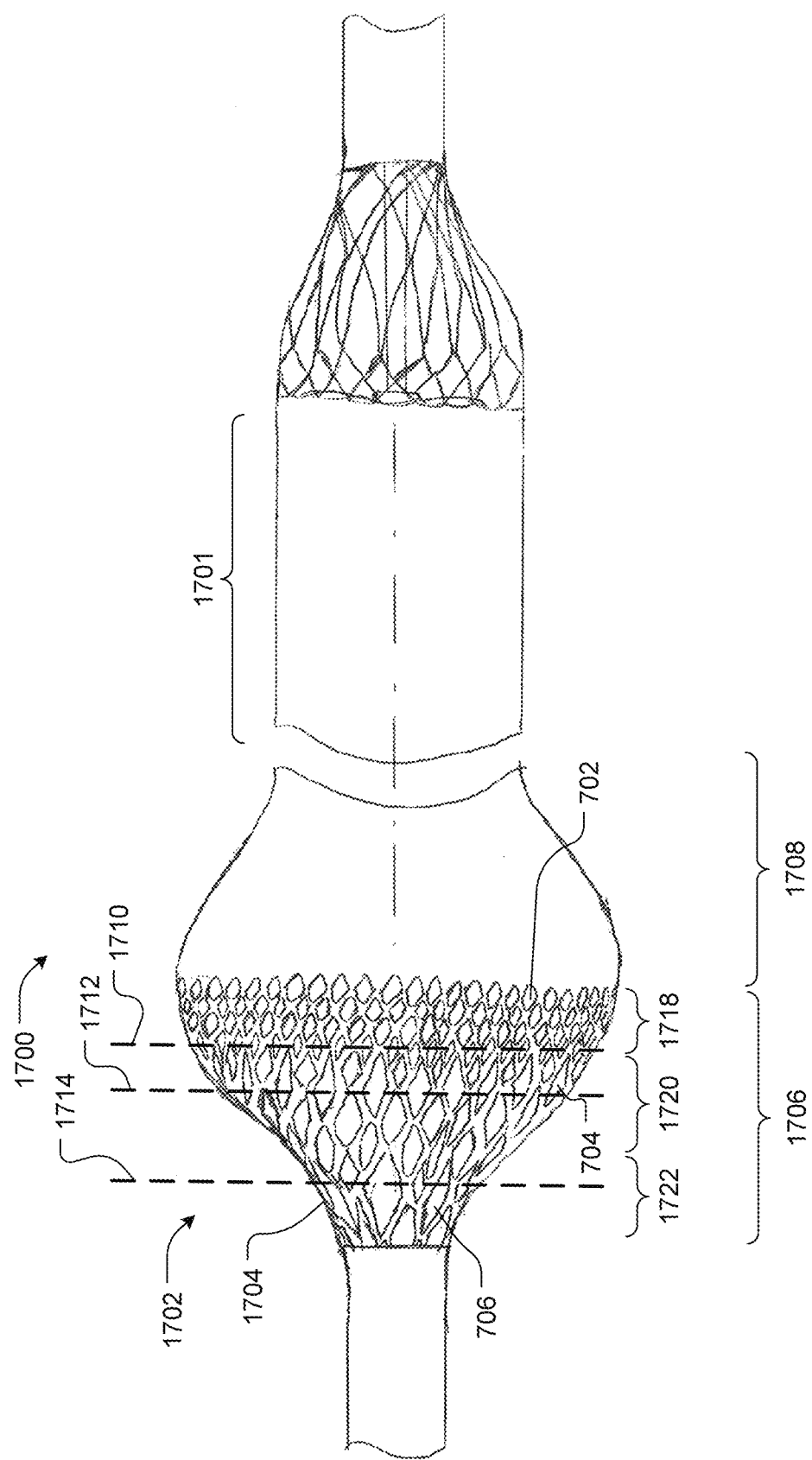
FIG. 17 is a side view of the distal end region of an expandable housing of FIGS. 10-11, with a long inflow cannula and a bulbous expandable filter having an enlarged inflow area installed thereon, according to another embodiment of the present invention.
Figure 18:
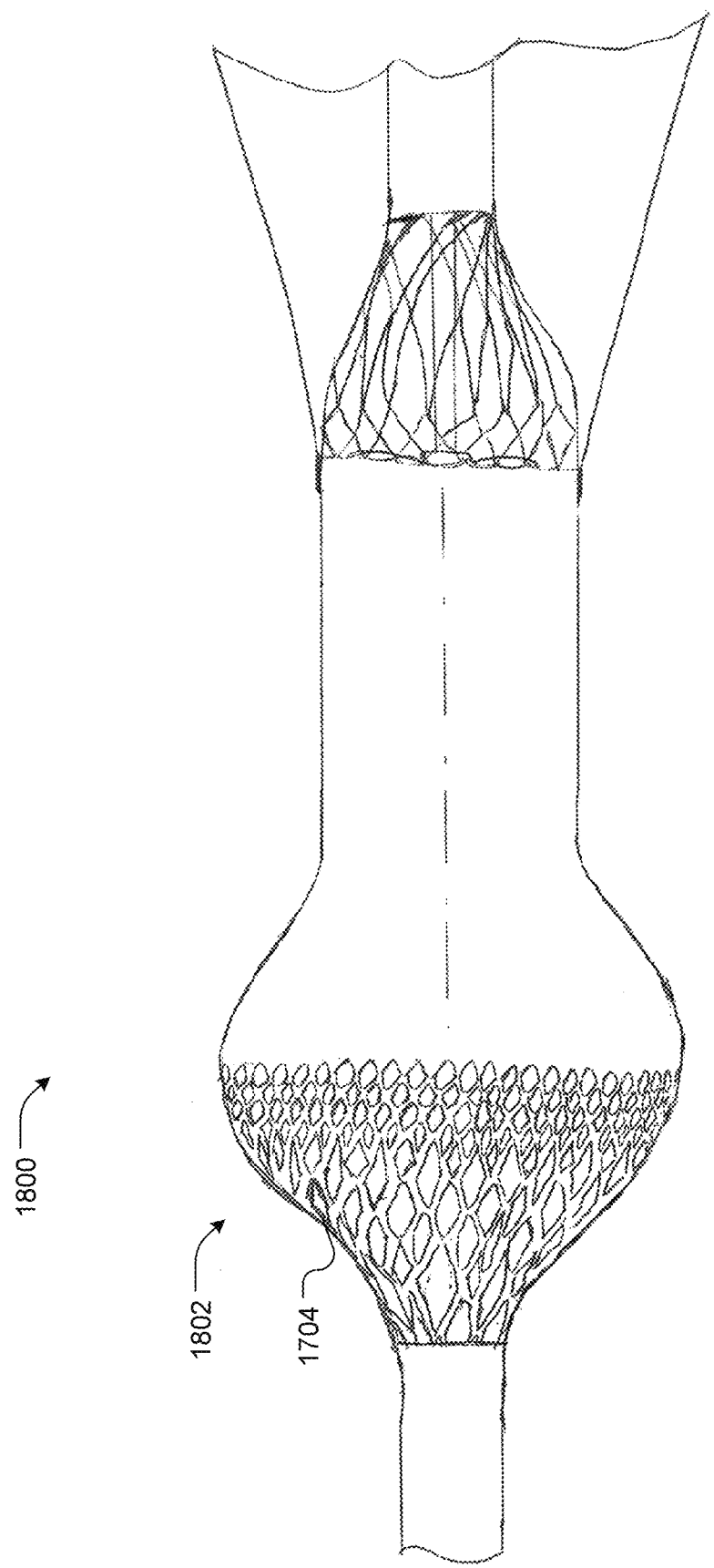
FIG. 18 is a side view of the distal end region of an expandable housing of FIGS. 10-11, with a downstream tubing, rather than a long inflow cannula, and a bulbous expandable filter having an enlarged inflow area installed thereon, according to another embodiment of the present invention.

FIG. 17 is a side view of the distal end region of an expandable housing of FIGS. 10-11, with a long inflow cannula 1701 and a bulbous expandable filter 1700 having an enlarged inflow area 1702 installed thereon. FIG. 18 is a side view of the distal end region of an expandable housing of FIGS. 10-11, with a downstream tubing, rather than a long inflow cannula, and a bulbous expandable filter 1800 having an enlarged inflow area 1800 installed thereon, but in other respects similar to FIG. 17.

The bulbous expandable filters 1700 and 1800 provide enlarged inflow areas 1702 and 1802 to the intravascular blood pump 100, which improves the flow characteristic of the pump. The enlarged inflow areas 1702 and 1802 are covered with a filter 1704 similar to FIGS. 10, 11 and 12, but with yet larger apertures.

The filter 130 includes a distal portion 1706 and a proximal portion 1708. The distal portion 1706 monotonically increases in diameter in a proximal direction along the longitudinal axis. The proximal portion 1708 monotonically decreases in diameter in the proximal direction along the longitudinal axis.

At least a portion of the plurality of apertures 702-706 is disposed on the distal portion 1706. In some embodiments, the proximal portion 1708 is devoid of apertures.

In general, sizes of the apertures of the plurality of apertures 702-706 increase along the longitudinal axis, in the distal direction, although the increase need not necessarily be monotonic. The apertures 702-706 are arranged in a plurality of generally circumferential, relative to the longitudinal axis, rows of equal-sized apertures, exemplified by rows 1710, 1712 and 1714. Ones of the rows 1710-1714 have different numbers of the apertures 702-706 from others of the rows 1710-1714. For example, a first row 1710 (indicated by a dashed line) of the plurality of generally circumferential rows comprises more apertures 702 than a second row 1712 of the plurality of generally circumferential rows. Each aperture 702 of the first row 1710 has a smaller area than each aperture 704 of the second row 1712.

The apertures 702-706 may be arranged in a plurality of generally circumferential, relative to the longitudinal axis, bands of about equal-sized apertures, exemplified by bands 1716, 1718 and 1720. Size of the apertures 702-706 in each of the plurality of bands 1718-1722 increases monotonically along the longitudinal axis. That is, in general, the apertures in band 1720 are larger than the apertures in band 1718. However, apertures in a given row may be larger or smaller than apertures in another row of the same band, because although the two rows have the same number of apertures, the two rows may have different circumferences. In the embodiment shown in FIG. 17, the size of the apertures 702-706 in each of the plurality of bands 1718-1722 increases monotonically along the longitudinal axis in the distal direction. Other aspects of the aperture sizes and arrangements are similar to those discussed with respect to FIG. 7.

As noted, the distal end region of the expandable housing shown in FIG. 18 is similar to that shown in FIG. 17, except that the expandable housing in FIG. 18 includes downstream tubing, rather than a long inflow cannula.

Figure 19:
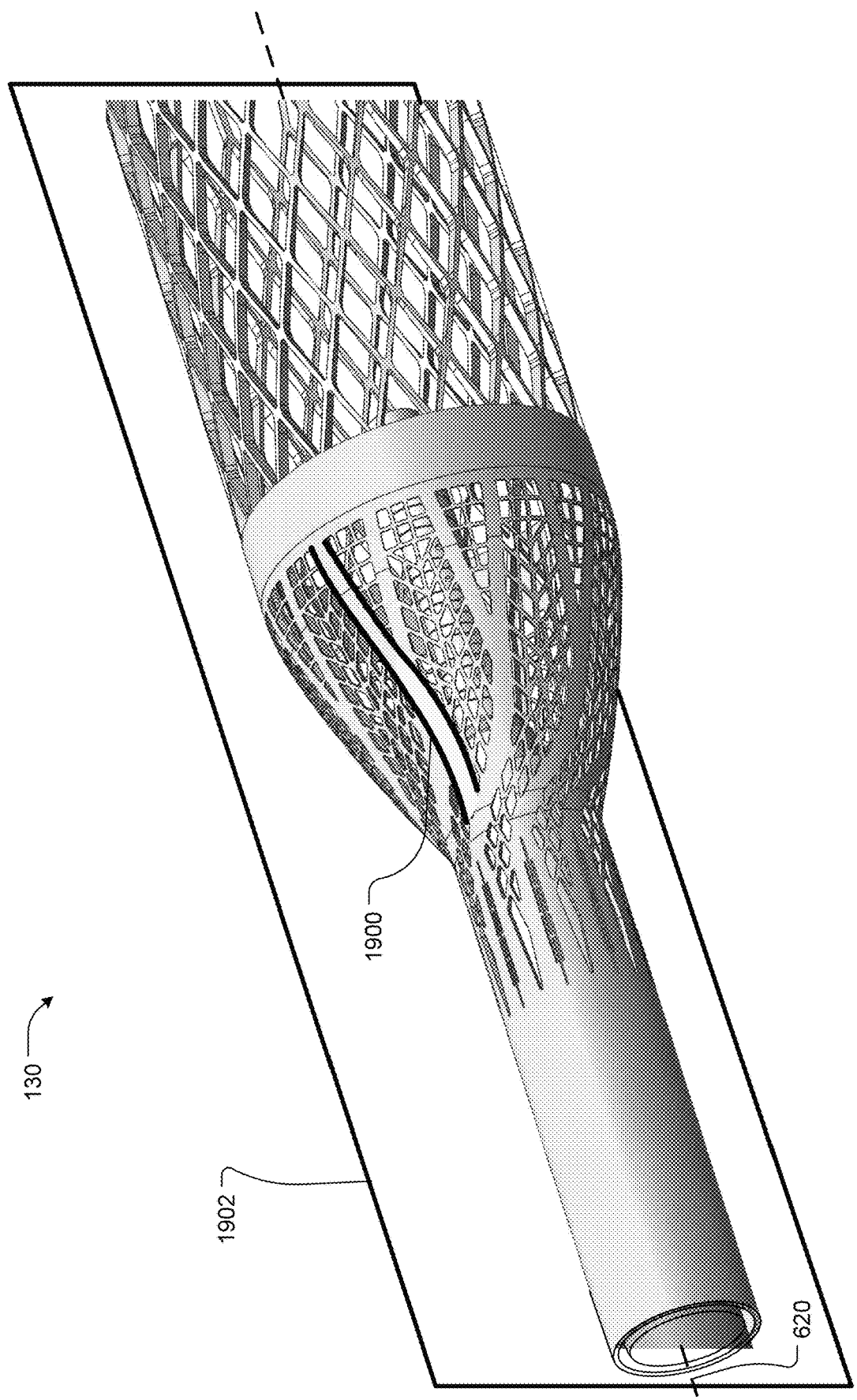
FIG. 19 shows a perspective view of an expandable filter formed of a mesh of filaments and mounted on a distal end region of the expandable housing (FIGS. 3-5) of the intravascular blood pump of FIGS. 1-2, similar to that of FIG. 6, but with some longitudinal struts, according to an embodiment of the present invention.

FIG. 19 is a perspective view of the distal end region of the expandable housing of FIGS. 10-11, with an expandable filter similar to that of FIG. 14, but with some longitudinal struts, exemplified by longitudinal strut 1900. Each longitudinal strut 1900 lies in a respective plane, exemplified by plane 1902, that contains the longitudinal axis 620. As used herein, the phrase a "plane that contains" a line means the line lies completely in the plane. Although FIG. 19 shows only one longitudinal strut 1900, the filter 130 may include additional longitudinal struts (not shown).

While the invention is described through the above-described exemplary embodiments, modifications to, and variations of, the illustrated embodiments may be made without departing from the inventive concepts disclosed herein. For example, although specific parameter values, such as dimensions and materials, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," are used to distinguish respective struts, rings of apertures and/or bands of apertures from one another and are not intended to indicate any particular order or total number of struts, rings of apertures and/or bands of apertures in any particular embodiment. Thus, for example, a given embodiment may include only a second struts, rings of apertures and/or bands of apertures and a third struts, rings of apertures and/or bands of apertures.

What is claimed is:

1. An intravascular blood pump, comprising:
   a catheter configured for insertion into a blood vessel, the blood vessel defining an interior volume, through which blood flows;
   a pump housing attached to the catheter and defining an input port and an output port, the pump housing having a longitudinal axis;
   an impeller disposed within the pump housing and configured, when rotated, to pump blood from the input port to the output port; and
   a filter configured to be mounted over an exterior of the pump housing, wherein the filter is in fluid communication between: (a) the interior volume of the blood vessel, external to the pump housing, and (b) the input port, the filter comprising a plurality of generally helical first struts wound about the longitudinal axis and a plurality of second struts, the plurality of generally helical first struts and the plurality of second struts collectively defining a plurality of apertures therebetween,
   wherein the filter comprises a tube having a wall, wherein the plurality of apertures comprises a plurality of openings defined through the wall, and
   wherein the filter comprises a distal filter portion and a proximal filter portion.

2. The intravascular blood pump according to claim 1, wherein the pump housing, the impeller and the filter are each alternatingly radially compressible and radially expandable.

3. The intravascular blood pump according to claim 2, wherein the pump housing is configured, when radially compressed, to longitudinally lengthen an amount that depends on an amount by which the pump housing is radially compressed, and the filter is configured, when radially compressed, to longitudinally lengthen an amount that depends on an amount by which the filter is radially compressed such that, for a given amount of radial compression, the filter and the pump housing longitudinally lengthen about equal amounts.

4. The intravascular blood pump according to claim 1, wherein the catheter, the pump housing, the impeller and the filter are configured for use in a living patient, such that each aperture of the plurality of apertures is sized to prevent ingestion, by the input port, of heart tissue of the living patient.

5. The intravascular blood pump according to claim 1, wherein each aperture of the plurality of apertures has a largest dimension less than or equal to about 0.5 mm or about 0.4 mm.

6. The intravascular blood pump according to claim 1, wherein each aperture of the plurality of apertures has an area less than or equal to about $0.09$ mm$^2$ or about $0.16$ mm$^2$.

7. The intravascular blood pump according to claim 1, wherein the plurality of apertures have a size that increases monotonically along the longitudinal axis.

8. The intravascular blood pump according to claim 1, wherein the plurality of generally helical first struts are wound clockwise about the longitudinal axis, and the plurality of second struts are generally helically wound counterclockwise about the longitudinal axis.

9. The intravascular blood pump according to claim 1, wherein the plurality of generally helical first struts are wound in a first direction about the longitudinal axis, and the plurality of second struts are generally helically wound in the first direction about the longitudinal axis.

10. The intravascular blood pump according to claim 1, wherein each aperture of at least a subset of the plurality of apertures has a general rhombus or rhomboid shape.

11. The intravascular blood pump according to claim 1, wherein the plurality of generally helical first struts comprise a plurality of first filaments, the plurality of second struts comprise a plurality of second filaments and the plurality of first filaments and the plurality of second filaments are woven together, such that the plurality of apertures is defined between respective adjacent plurality of first filaments and plurality of second filaments.

12. The intravascular blood pump according to claim 1, wherein the tube comprises a generally funnel-shaped tube.

13. The intravascular blood pump according to claim 1, wherein the wall is about 10-100 μm thick.

14. The intravascular blood pump according to claim 1, wherein the pump housing comprises a plurality of third struts that collectively define a plurality of third apertures therebetween, and at least some of the plurality of generally helical first struts and the plurality of second struts register radially over respective ones of the plurality of third struts.

15. The intravascular blood pump according to claim 1, wherein each strut of at least a subset of the plurality of generally helical first struts comprises a fork that includes a plurality of tines, wherein the at least a subset of the plurality of generally helical first struts and the at least a subset of the plurality of second struts extend between a pair of the tines and collectively define a plurality of the apertures therebetween.

16. The intravascular blood pump according to claim 15, wherein each strut of at least a subset of the plurality of generally helical first struts that comprises a fork is wider than each of the plurality of generally helical first struts that does not comprise a fork.

17. The intravascular blood pump according to claim 1, wherein the plurality of apertures are arranged in a plurality of generally circumferential rows of equal-sized apertures, relative to the longitudinal axis, wherein ones of the plurality of generally circumferential rows have different numbers of apertures from others of the plurality of generally circumferential rows.

18. The intravascular blood pump according to claim 17, wherein a first row of the plurality of generally circumferential rows comprises more apertures than a second row of the plurality of generally circumferential rows, and each aperture of the first row of the plurality of generally circumferential rows has a smaller area than each aperture of the second row of the plurality of generally circumferential rows.

19. The intravascular blood pump according to claim 1, wherein the apertures are arranged in a plurality of generally circumferential bands of about equal-sized apertures, relative to the longitudinal axis, wherein size of the apertures in each of the plurality of generally circumferential bands increases monotonically along the longitudinal axis.

20. The intravascular blood pump according to claim 19, wherein the distal filter portion monotonically increases in diameter in a proximal direction along the longitudinal axis, the proximal filter portion monotonically decreases in diameter in the proximal direction along the longitudinal axis and at least a portion of the plurality of apertures is disposed on the distal filter portion.

* * * * *